(12) United States Patent
Howlett et al.

(10) Patent No.: US 7,604,632 B2
(45) Date of Patent: Oct. 20, 2009

(54) CRYOSURGERY DEVICE

(75) Inventors: Harold A. Howlett, Horn Lake, MS (US); Robert C. Johnson, Memphis, TN (US); Charles E. Lundy, Jr., Germantown, TN (US); Eric Chen-nan Su, Collierville, TN (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 583 days.

(21) Appl. No.: 11/222,353

(22) Filed: Sep. 8, 2005

(65) Prior Publication Data

US 2006/0189968 A1 Aug. 24, 2006

Related U.S. Application Data

(63) Continuation-in-part of application No. 10/643,301, filed on Aug. 19, 2003, now abandoned.

(51) Int. Cl.
*A61B 18/02* (2006.01)
(52) U.S. Cl. ........................................................ 606/25
(58) Field of Classification Search ............. 606/20–26; 222/402.1, 402.13; 251/353; 277/945
See application file for complete search history.

(56) References Cited

U.S. PATENT DOCUMENTS

| | | | |
|---|---|---|---|
| 3,938,898 A * | 2/1976 | Reitknecht | 401/183 |
| 3,946,911 A * | 3/1976 | Morane et al. | 222/402.11 |
| 4,082,096 A | 4/1978 | Benson | |
| 4,367,743 A | 1/1983 | Gregory | |
| 4,865,028 A | 9/1989 | Swart | |
| 5,042,261 A * | 8/1991 | Yeakel et al. | 62/64 |
| 5,200,170 A | 4/1993 | McDow | |
| 5,286,720 A | 2/1994 | Niedbala et al. | |
| 5,330,745 A | 7/1994 | McDow | |
| 5,516,505 A | 5/1996 | McDow | |
| 5,549,228 A * | 8/1996 | Brown | 222/570 |
| 5,738,682 A | 4/1998 | Jensma | |
| 6,039,306 A | 3/2000 | Pericard et al. | |
| 6,092,527 A | 7/2000 | Jensma | |
| 6,296,410 B1 | 10/2001 | Ruizendaal | |

(Continued)

OTHER PUBLICATIONS

Complaint Jul. 23, 2004; Civil Action No. 04-3507.

(Continued)

*Primary Examiner*—Michael Peffley
*Assistant Examiner*—Ronald J Hupczey, Jr.
(74) *Attorney, Agent, or Firm*—Matthew J. Golden

(57) ABSTRACT

A cryosurgery device includes an aerosol container holding a liquid refrigerant and having a valve and a stem extending out therefrom; an actuator seated on the stem and including an outlet tube for receiving released refrigerant from the container; a hub mounted on the container and including slots therein; and a base having a central opening for receiving the hub, the base including aligning projections that enter the slots in the hub to engage and apply pressure to the actuator to cause the actuator to depress the stem and release refrigerant into the base. The container may further contain an applicator tube mounted to the hub in fluid communication with the outlet tube with a porous tip mounted to a distal end of the applicator tube for receiving the refrigerant and, being chilled thereby, applied to a skin lesion to be treated.

12 Claims, 27 Drawing Sheets

U.S. PATENT DOCUMENTS 6,318,603 B1 11/2001 Burt
6,375,652 B1 4/2002 Griswold
6,387,090 B1 * 5/2002 Jensma ..................... 606/23

OTHER PUBLICATIONS

Defendant's Answer and Counterclaims Aug. 18, 2004; Civil Action No. 04 CV 3507.
Declaration of R. Sam Niedbala Aug. 18, 2004; Civil Action No. 2:04-CV-03507-NS.
Declaration of Keith W. Kardos Aug. 2004; Civil Action No. 2:04-CV-03507-NS.
Orasure Motion for Preliminary & Memorandum of Law Aug. 19, 2004.
Schering-Plough Opposition to Motion for Preliminary Injunction Sep. 17, 2004; Civil Action No. 04 CV 3507.
Declaration of Dr. Charles Lundy Sep. 16, 2004; Civil Action No. 04 CV 3507.
Declaration of Fred Duchin Sep. 17, 2004; Civil Action No. 04 CV 3507.
Declaration of Christine Jarvis Sep. 16, 2004; Civil Action No. 04 CV 3507.
Declaration of Nancy Miller-Rich Sep. 19, 2004; Civil Action No. 04 CV 3507.
Orasure Memorandum of Law on Claim Construction Nov. 15, 2004; Civil Action No. 2:04-CV-03507-NS.
Schering-Plough Memorandum of Law on Claim Construction Nov. 15, 2004; Civil Action No. 04 CV 3507.
Schering-Plough First Amended Counterclaims May 3, 2005; Civil Action No. 04 CV 3507.
Orasure Answer to Amended Couterclaim May 11, 2005; Civil Action No. 2:04-CV-03507-NS.
District Court Claim Construction Memorandum and Order Jul. 6, 2005; Civil Action No. 04-CV-3507.
Orasure Motion for Reconsideration of Claim Construction Order Jul. 20, 2005; Civil Action No. 2:04-CV-03507-NS.
Schering-Plough Motion for Reconsideration of Claim Construction Order Jul. 22, 2005; Civil Action No. 04 CV 3507.
Schering-Plough Opposition to Orasure Motion for Reconsideration of Claim Construction Order Jul. 27, 2005.
Orasure Opposition to Schering-Plough Motion for Reconsideration Order Aug. 1, 2005; Civil Action No. 2:04-CV-03507-NS.
District Court Order upon Motion for Reconsideration Order Aug. 12, 2005; Civil Action No. 04-3507.
NAD/CARU Case Reports 3-4/07 pp. 143-145.

* cited by examiner

CRYOSURGERY DEVICE

This application is a continuation-in-part application of U.S. application Ser. No. 10/643,301, filed Aug. 19, 2003, the contents of which are hereby incorporated in their entirety into the present specification.

INTRODUCTION TO THE INVENTION

The present invention relates generally to a cryosurgery device for cryogenically treating skin lesions and, more particularly, is directed to a cryosurgery device for applying a cryogenic refrigerant from a pressurized container to a porous-tip applicator which contacts the area of the skin lesion to freeze the skin lesion.

Historically, physicians have used liquid nitrogen applications to remove lesions from the skin. This has been very effective, but suffers from the disadvantage of requiring specialized equipment to condense nitrogen, the need for specialized storage devices, and the inherent hazards of handling and dispensing a material having a boiling point of −196° C. A certain amount of skill is required during treatment, so that excessive tissue injury is not obtained.

More recently, methods were developed to treat skin lesions cryogenically by employing a liquid refrigerant contained in a pressurized container. In such methods, an effective amount of the cryogenic agent from the pressurized container is supplied into a hollow supply tube, having a cotton or plastic foam applicator located at the distal end of the tube, so that the cryogenic material accumulates in the applicator. The skin surface of the lesion is then contacted with the applicator having the accumulated cryogenic agent for a period of time sufficient to permit the cryogenic agent to reduce the temperature of the skin lesion tissue to temperatures that freeze the skin, such that permanent, irreversible rupture of cellular membranes of cells of the skin lesion occurs while the cryogenic agent is evaporating. Subsequently, the applicator is removed from the skin surface after a period of time that is generally about 20 to about 60 seconds, depending on the boiling point of the refrigerant and the depth of tissue that will be frozen, and the frozen skin tissue of the skin lesion is then permitted to slowly thaw. During the next several weeks, the tissue that was frozen dislodges from the surrounding skin.

Examples of devices for applying a cryogenic agent to a skin lesion are disclosed in U.S. Pat. No. 4,865,028 (Swart); U.S. Pat. No. 5,516,505 (McDow); U.S. Pat. No. 5,200,170 (McDow); U.S. Pat. No. 5,330,745 (McDow); U.S. Pat. No. 5,738,682 (Jensma); U.S. Pat. No. 6,092,527 (Jensma); U.S. Pat. No. 6,296,410 (Ruizendaal); and U.S. Pat. No. 6,387,090 (Jensma).

A problem with such devices is the manner in which the cryogenic agent is moved from the container to the applicator. It is important that there be little loss in the cryogenic material during such transfer and, therefore, that the cryogenic material travels the most effective and shortest path in order to provide the greatest effectiveness in treating the skin lesion. Further, it is necessary to prevent accidental release of the cryogenic material to conserve the cryogenic agent, and to prevent injury to a user of the device.

SUMMARY OF THE INVENTION

Accordingly, it is a feature of the present invention to provide a cryosurgery device for freezing a skin lesion that overcomes the aforementioned problems.

It is another feature of the present invention to provide a cryosurgery device for freezing a skin lesion that provides an accurate and controlled supply of the cryogenic refrigerant.

It is still another feature of the present invention to provide a cryosurgery device for freezing a skin lesion that reduces waste of cryogenic agent.

It is yet another feature of the present invention to provide a cryosurgery device for freezing a skin lesion that substantially reduces potentially dangerous conditions from occurring during an uncontrolled escape of the cryogenic agent.

It is a further feature of the present invention to provide a cryosurgery device for freezing a skin lesion in which the cryogenic material travels the most effective and shortest path to the applicator tip.

It is a still further feature of the present invention to provide a cryosurgery device for freezing a skin lesion that is economical to manufacture and easy to use by consumers.

In accordance with an embodiment of the present invention, a cryosurgery device for use with an aerosol container of the type having a valve and a stem extending outward from the valve and the container, the container holding a propellant refrigerant therein, includes an actuator adapted to seat on a stem of the valve in order to depress the stem and release refrigerant from the container. The actuator includes an outlet tube for receiving the released refrigerant from the container. A hub is adapted to mount on the container, the hub including at least one opening therein and a first aligning arrangement. An applicator tube is mounted to the hub in fluid communication with the outlet tube of the actuator, and a porous tip is mounted to a distal end of the applicator tube for receiving the refrigerant. A base has a central opening for receiving the hub and applicator tube therein. The base includes at least one key and a second aligning arrangement for cooperating with the first aligning arrangement such that the at least one key enters the at least one opening in the hub to engage and apply pressure to the actuator to cause the actuator to depress the valve stem and release the refrigerant.

The actuator includes an inlet tube connected with the main body and adapted to receive the stem of the valve therein, and a main body that connects together the inlet tube and the outlet tube in fluid communication with each other. The main body includes an arrangement for limiting insertion of the stem into the inlet tube, and an actuating surface against which at least one key engages, such that application of the pressure to the actuating surface causes the actuator to move such that the shoulder engages and depresses the stem to release the refrigerant. The main body includes a generally cylindrical side wall, a bottom wall which closes the side wall and which includes an opening, with the inlet tube and outlet tube being connected to opposite sides of the bottom wall in surrounding relation to the opening therein, and a ledge connected with an upper edge of the side wall, the ledge defining the actuating surface. The main body further includes reinforcing ribs on an outer surface of the side wall and connected with the ledge.

The applicator tube includes an enlarged diameter section at a distal end thereof for receiving the porous tip therein. The hub includes a securing arrangement for releasably securing the applicator tube thereto. Specifically, the applicator tube includes at least one projection extending outwardly from a lower end thereof, and the securing arrangement includes a threaded securing arrangement for threadedly receiving the at least one projection of the applicator tube in a releasable securing manner. The threaded securing arrangement includes an annular boss extending from an upper surface of the hub, a tube coaxially positioned within the annular boss and connected with the annular boss at a lower end thereof, and at least one helical thread on an inner surface of the annular boss for receiving the at least one projection in a threaded releasable securing manner. The tube of the hub is in axial alignment with the applicator tube and the outlet tube of the actuator. The hub includes a cylindrical side wall, and a top wall that closes an upper end of the cylindrical side wall, the top wall having an opening therein and the annular boss extends from an underside of the top wall as the upper surface of the hub in surrounding relation to the opening therein. Further, the at least one opening is in the top wall. In one embodiment, the applicator tube further includes a plurality of grooves through which the refrigerant flows.

The hub also includes a securing arrangement at a lower end of the cylindrical side wall adapted to be snap-fit secured over an upper annular lip of the container.

The first aligning arrangement includes at least one aligning rib on the cylindrical side wall, and the second aligning arrangement includes at least one recess for receiving the at least one aligning rib to angularly align the hub with the base. The opening in the base is closed by a lower wall at a lower end thereof.

The base includes at least one inwardly extending projection, each having an upper surface on which one the key is mounted, and each the upper surface defining a limit as to an extent to which the hub can be inserted into the base. For example, there can be three projections and keys of the base and three openings of the hub.

In accordance with another embodiment of the present invention, a cryosurgery device includes a container for holding a propellant refrigerant, the container including a valve and a stem extending out from the valve and the container; an actuator seated on the stem of the valve in order to depress the stem and release the refrigerant from the container, the actuator including an outlet tube for receiving the released refrigerant from the container; a hub mounted on the container, the hub including at least one opening therein and a first aligning arrangement; an applicator tube mounted to the hub in fluid communication with the outlet tube of the actuator; a porous tip mounted to a distal end of the applicator tube to be contacted by the refrigerant; and a base having a central opening for receiving the hub and applicator tube therein, the base including at least one key and a second aligning arrangement for cooperating with the first aligning arrangement such that the at least one key enters the at least one opening in the hub to engage and apply pressure to the actuator to cause the actuator to depress the stem and release the refrigerant.

A cryosurgery device can be used to treat a skin lesion, by: mounting an applicator tube and porous tip assembly to the hub, positioning the device over the base such that the base is located below the container and the porous tip extends downwardly into a central opening of the base; applying a force to the container, the base, or both, such that the keys enter corresponding openings in the hub to apply pressure to the actuator and cause refrigerant to be released into the applicator tube; discontinuing the force after a period of time sufficient for the liquid refrigerant to chill the porous tip to a therapeutically effective temperature; removing the base; and, without removing the applicator tube and porous tip from the hub, promptly placing the porous tip in contact with a lesion to cause freezing of the lesion.

Those of ordinary skill in the art will find alternative ways for operating the cryogenic device of the invention based on the description of the device in this application. Such methods are contemplated to be within the scope of the invention. For example, the cryogenic device can be operated in a way that does not require the use of an applicator tube mounted to the hub. In one embodiment of such a method, the cryogenic device is operated the same as described previously, but without the applicator tube mounted to the hub, the liquid refrigerant is now dispersed directly into the base where it collects in a pool. A separate applicator that will withstand the temperatures of the liquid refrigerant, for example a metal or polymer rod, with or without a porous tip, can then be immersed in the refrigerant and chilled to therapeutically effective temperature and then applied to a lesion to cause freezing of the lesion.

The above and other aspects, features, and advantages of the invention will become readily apparent from the following detailed description thereof, which is to be read in connection with the accompanying drawings.

DETAILED DESCRIPTION

Figure 1:
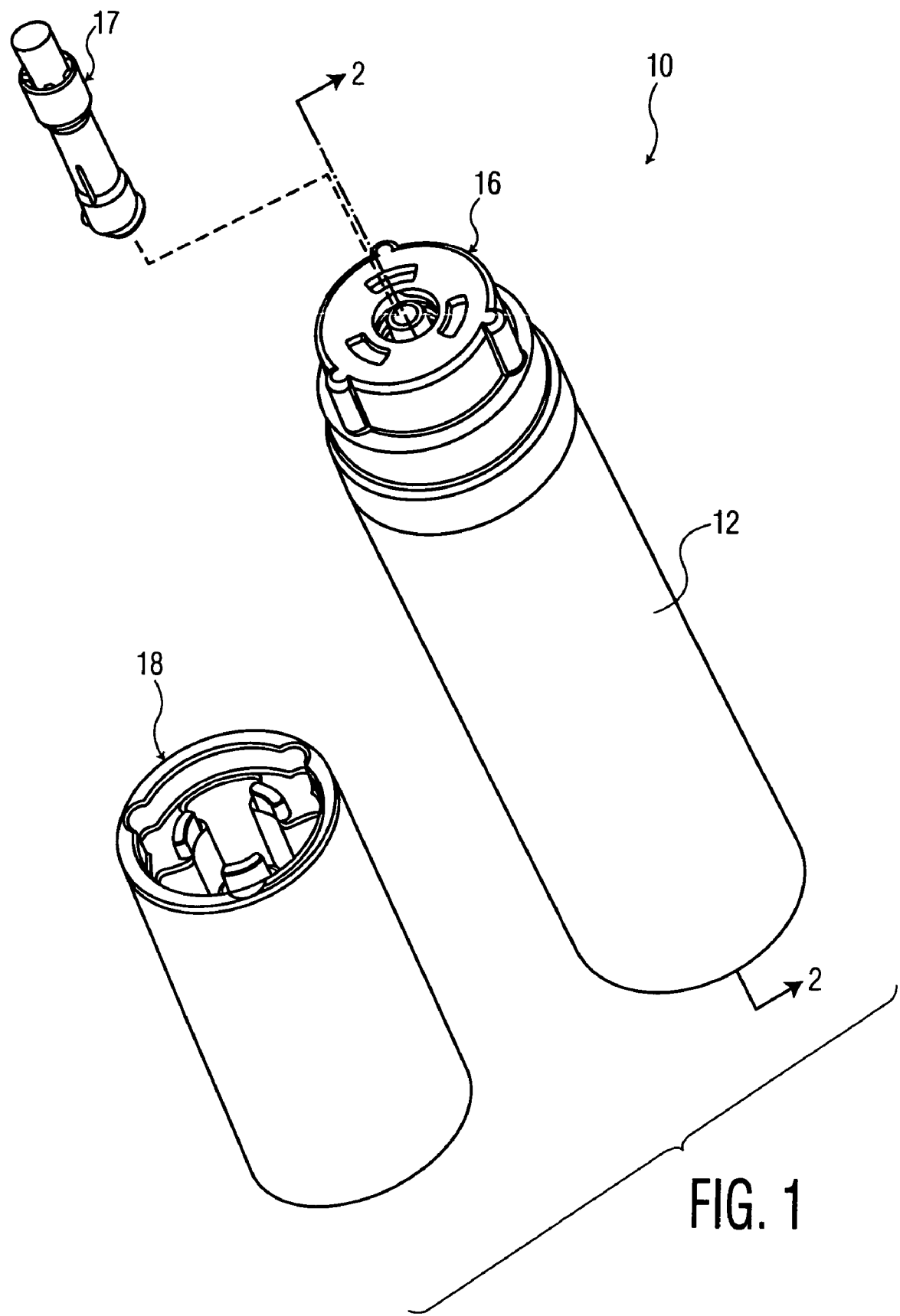
FIG. 1 is an exploded perspective view of a cryosurgery device according to the present invention.
Figure 2:
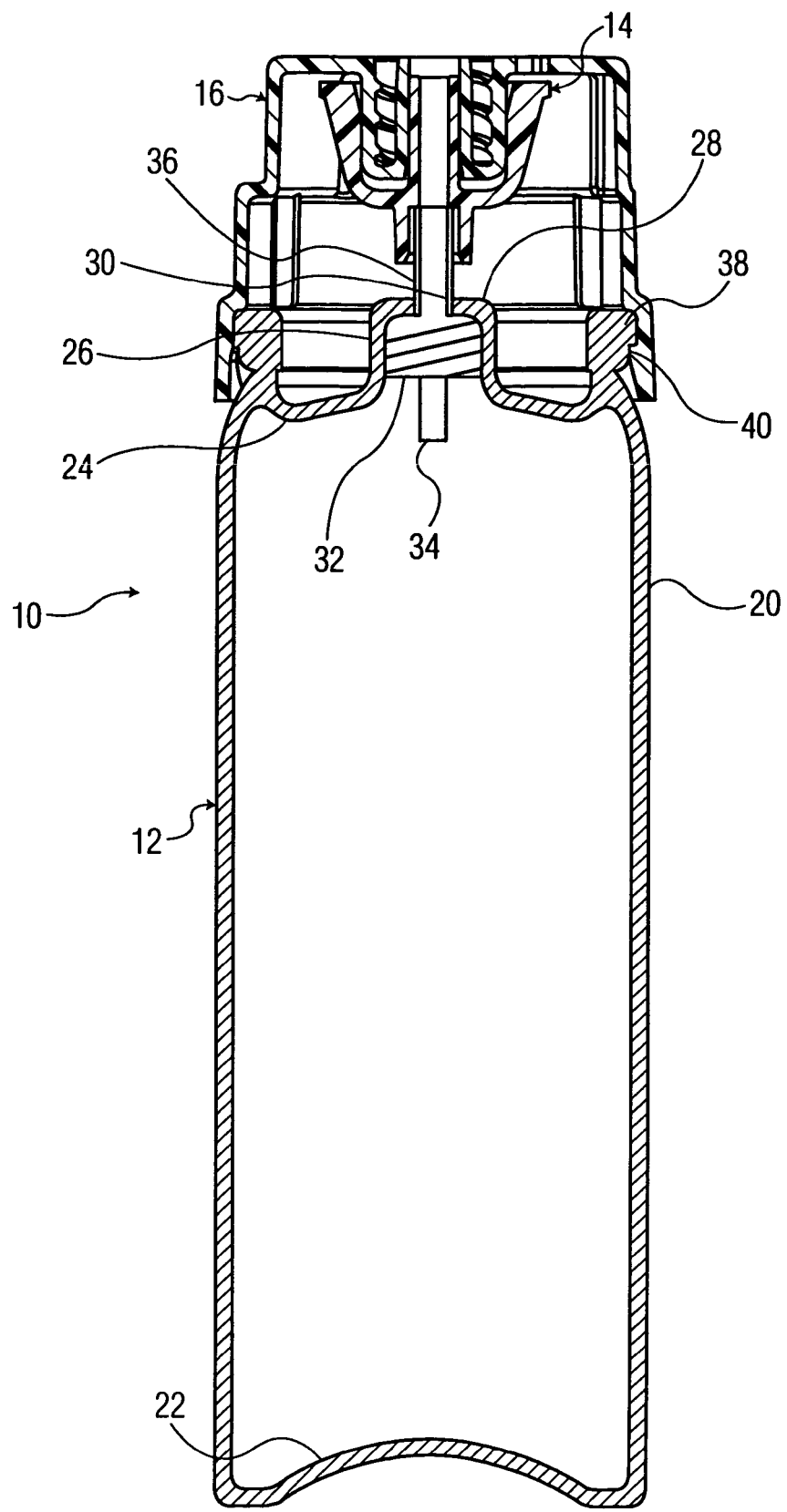
FIG. 2 is a cross-sectional view of a portion of the cryosurgery device of FIG. 1, taken along line 2-2 thereof.
Figure 3:
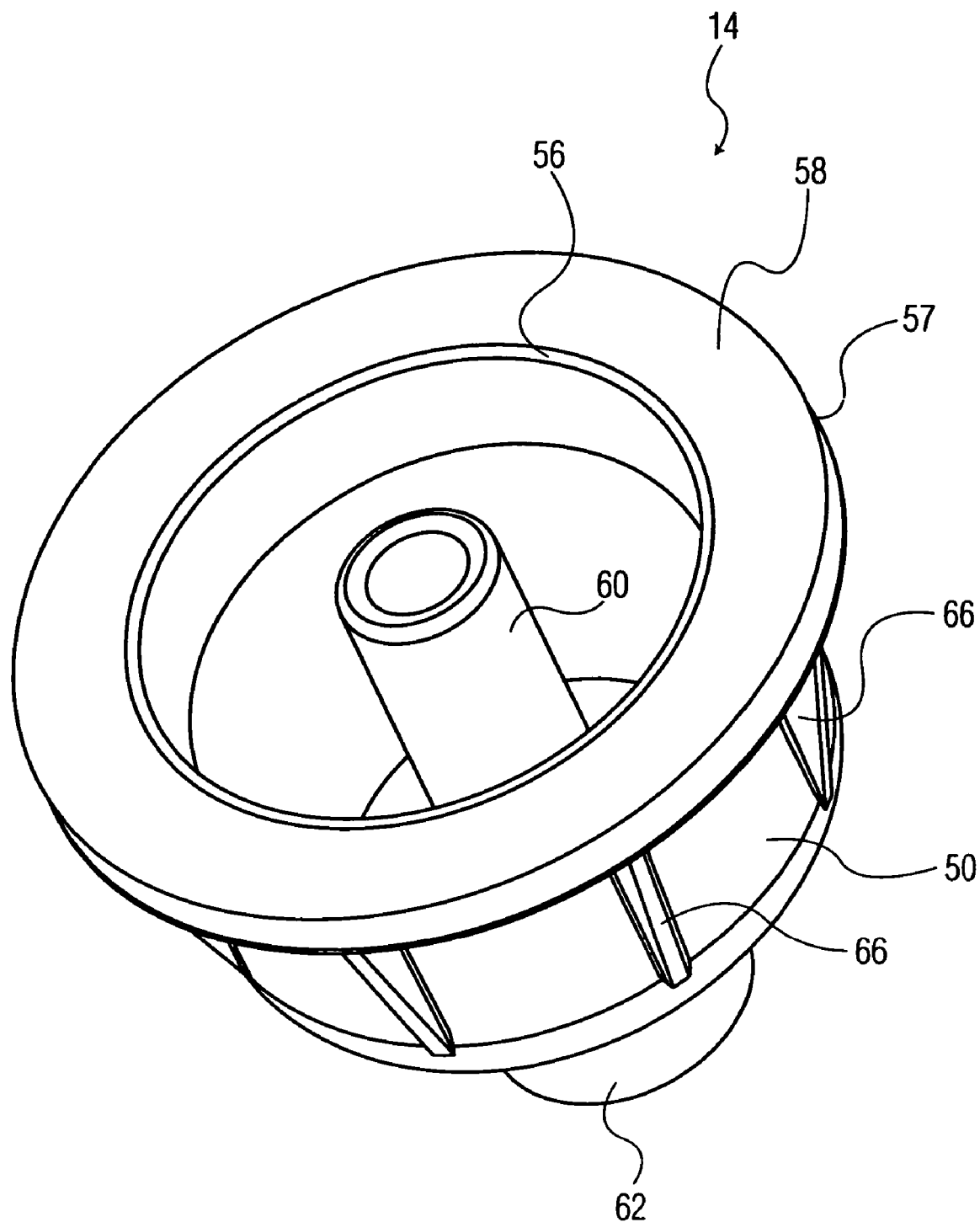
FIG. 3 is a perspective view of the actuation cup.
Figure 4:
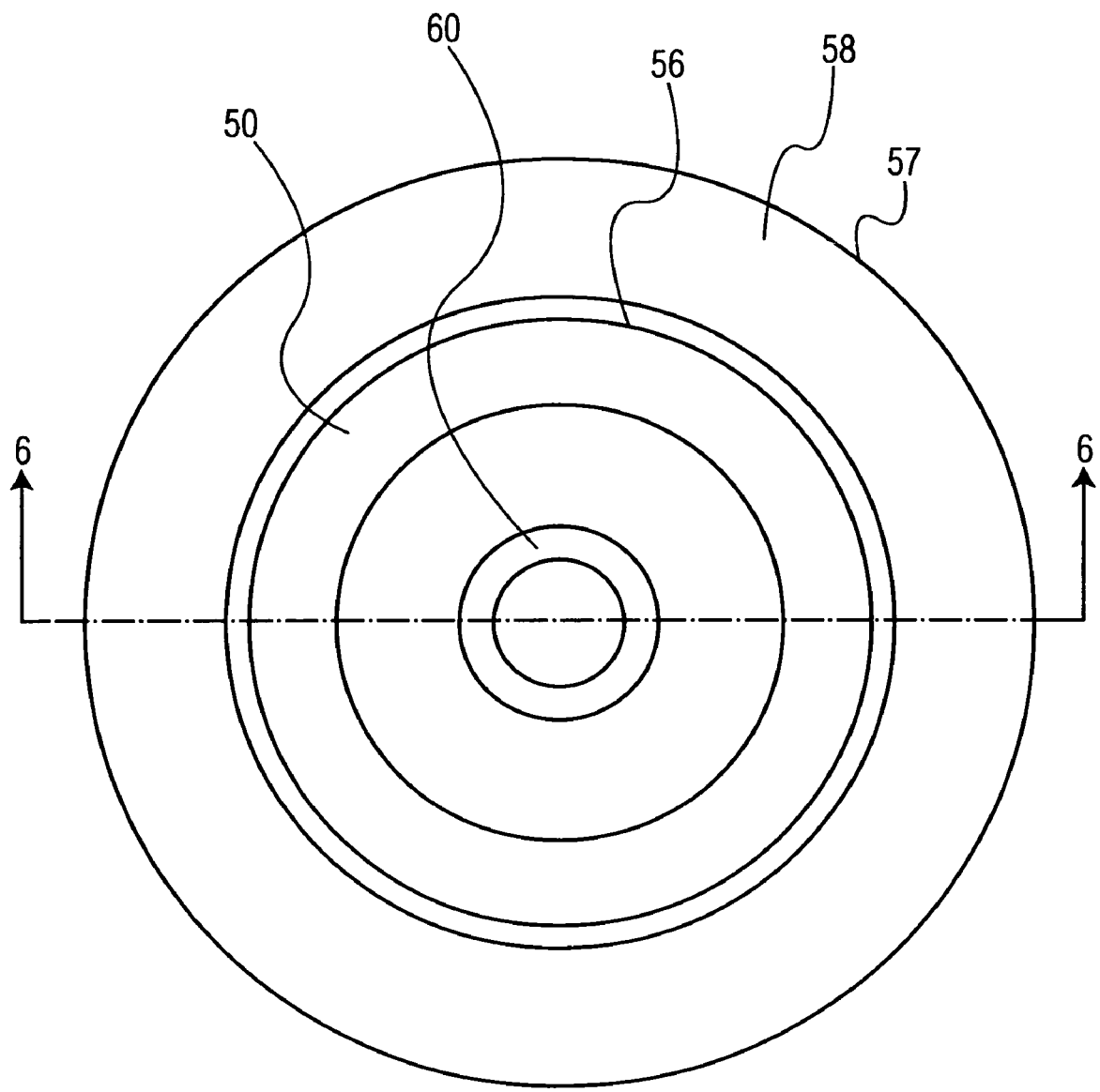
FIG. 4 is a top plan view of the actuation cup.
Figure 5:
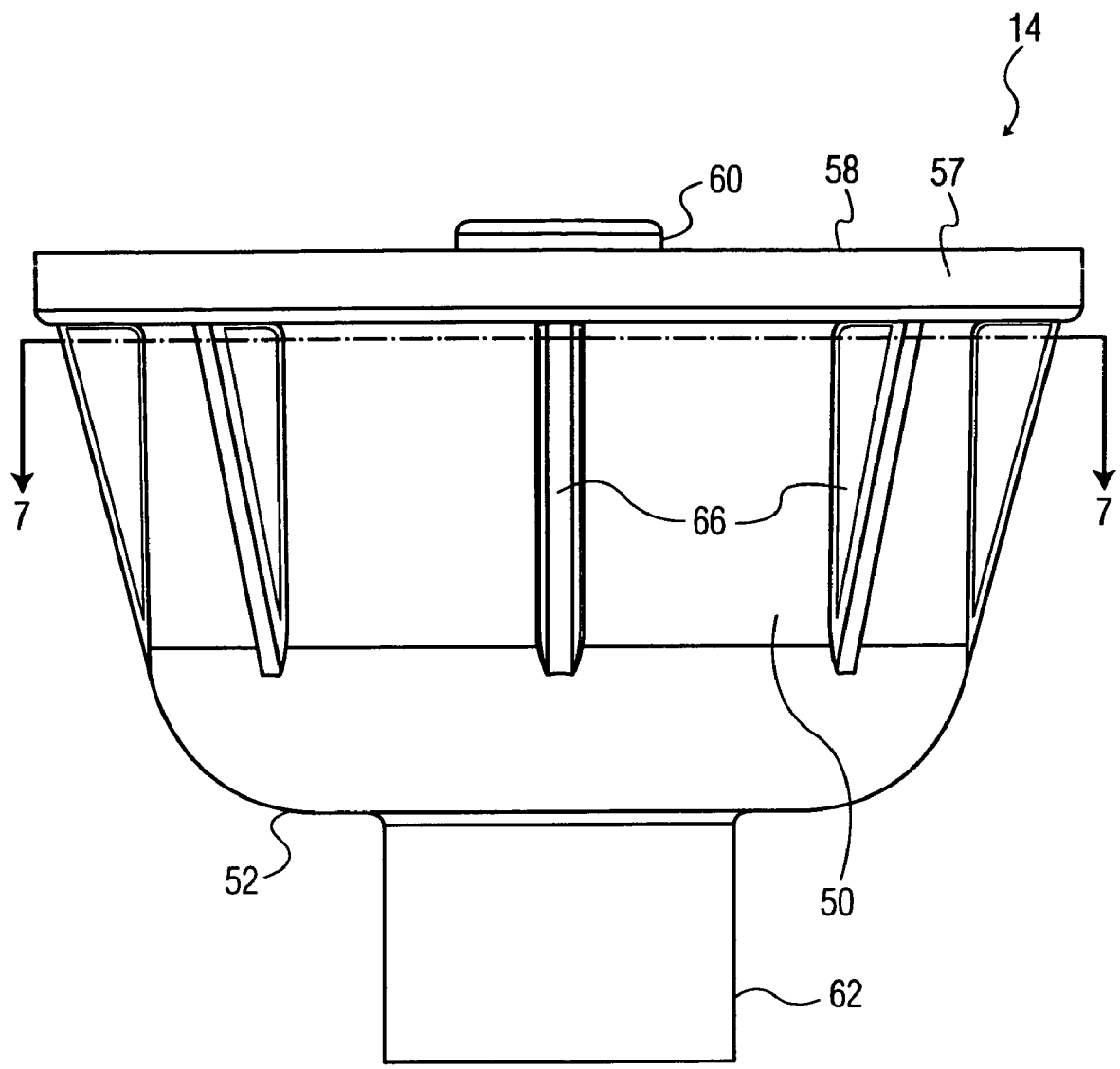
FIG. 5 is an elevational view of the actuation cup.
Figure 6:
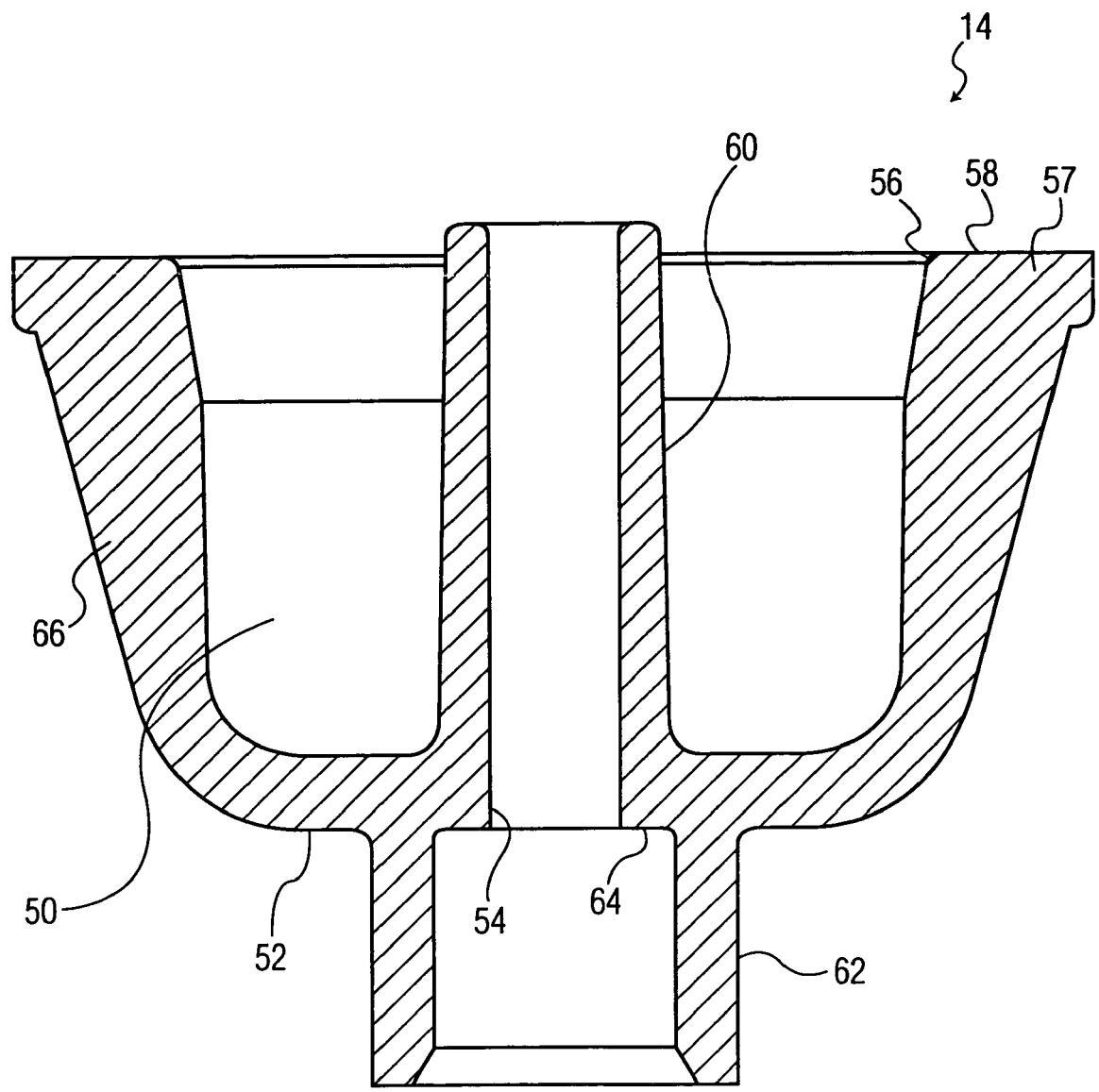
FIG. 6 is a cross-sectional view of the actuation cup, taken along line 6-6 of FIG. 4.
Figure 7:
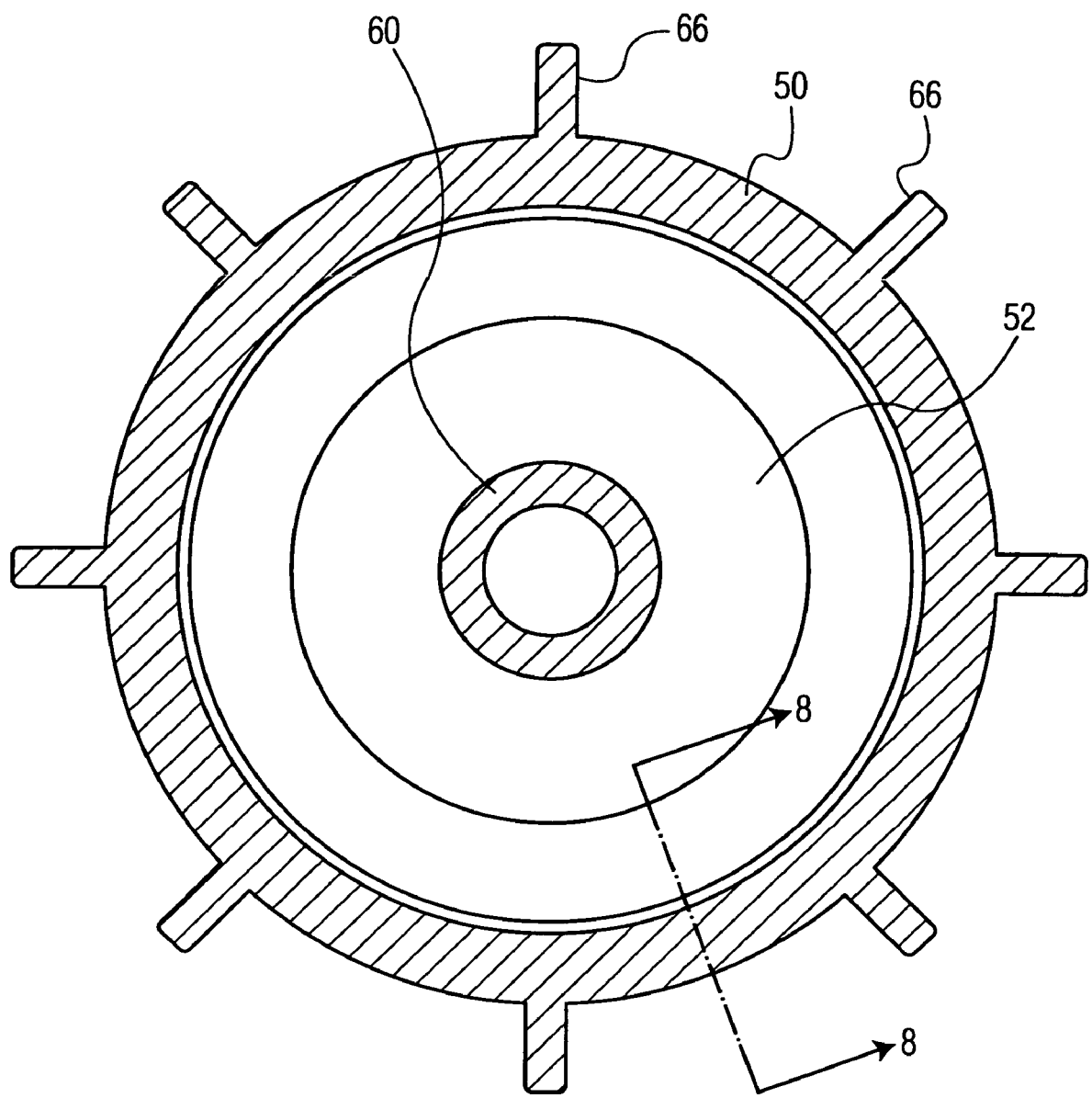
FIG. 7 is a cross-sectional view of the actuation cup, taken along line 7-7 of FIG. 5.
Figure 8:
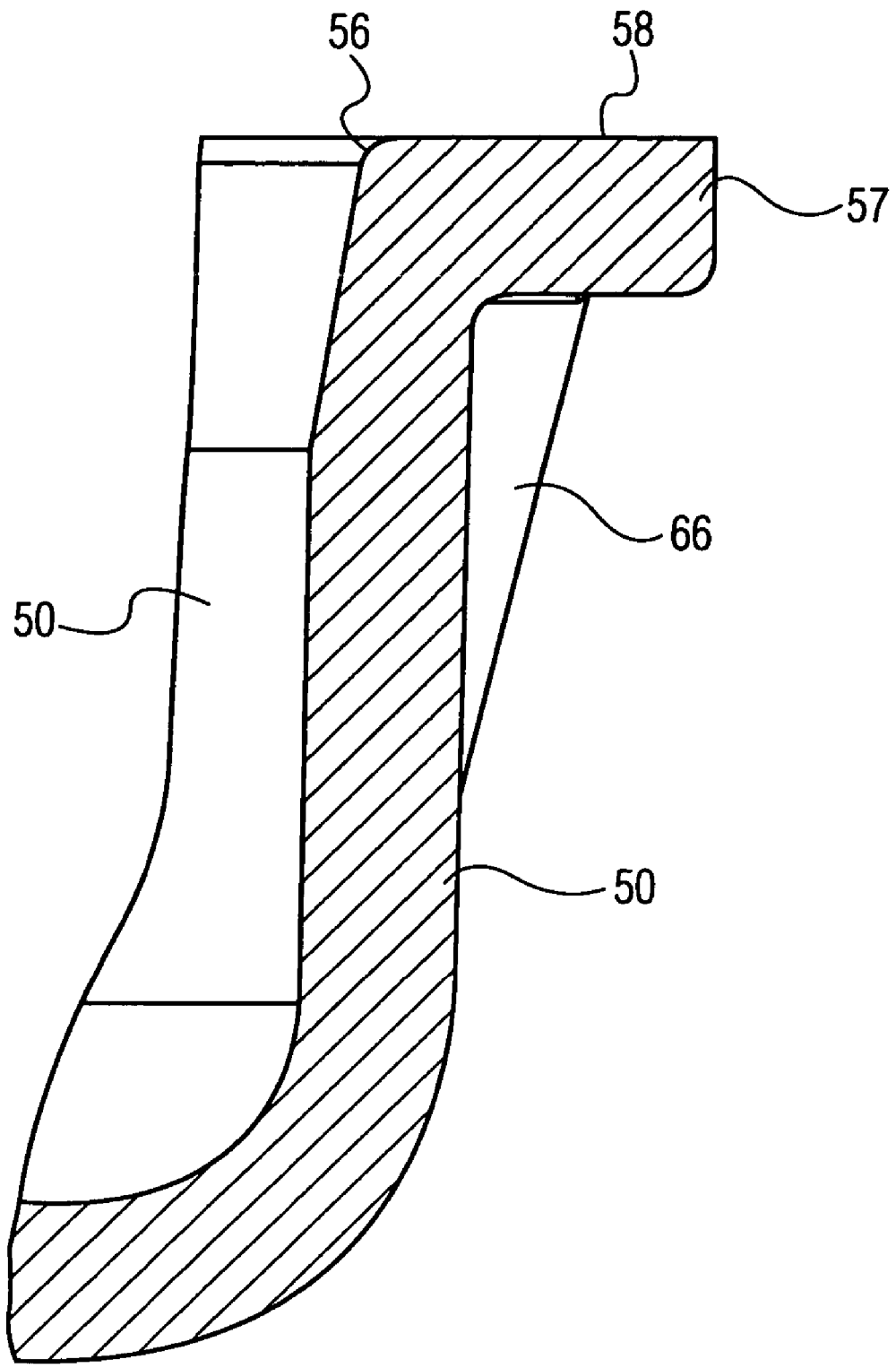
FIG. 8 is a cross-sectional view of the actuation cup, taken along line 8-8 of FIG. 7.
Figure 9:
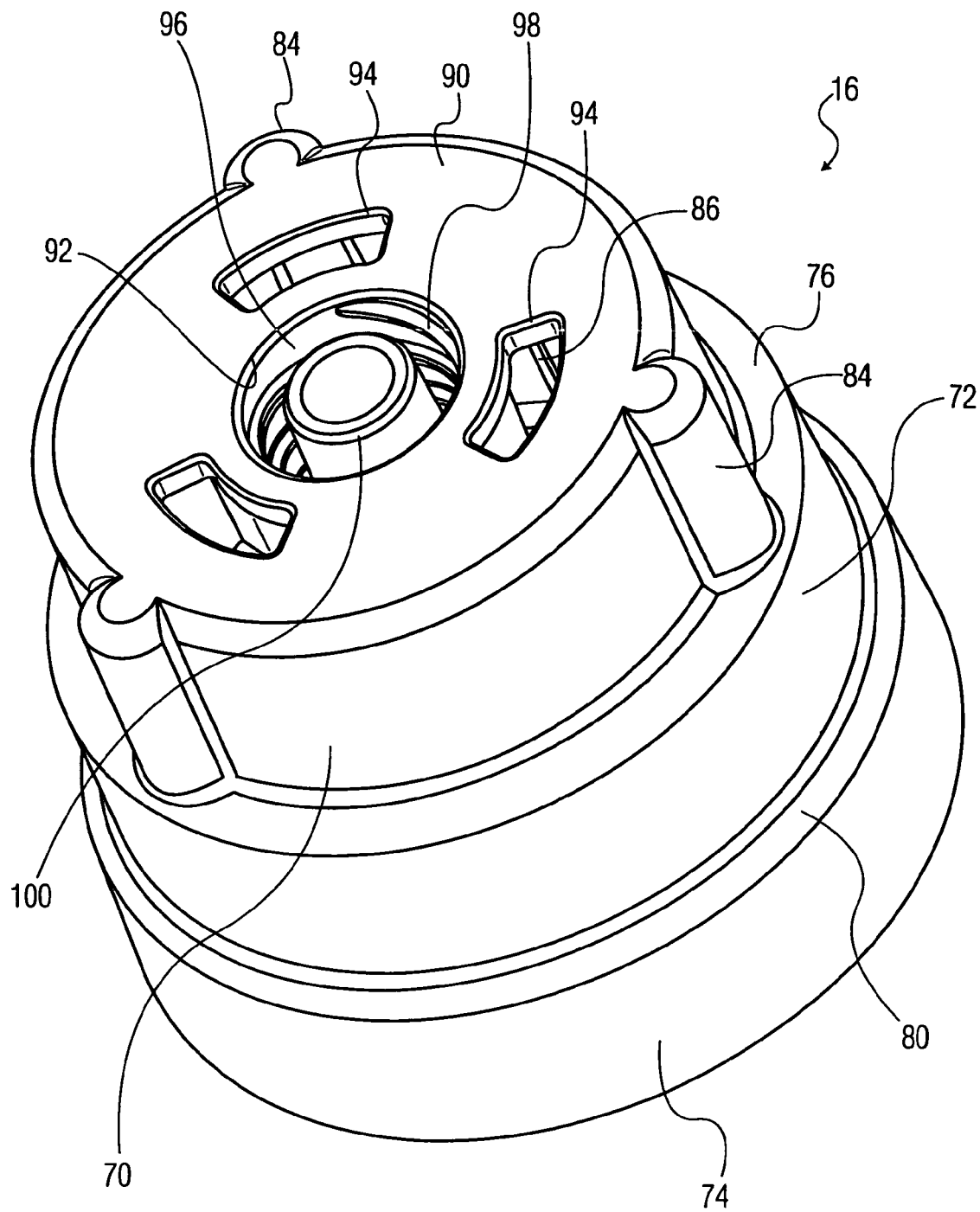
FIG. 9 is a perspective view of the hub.
Figure 10:
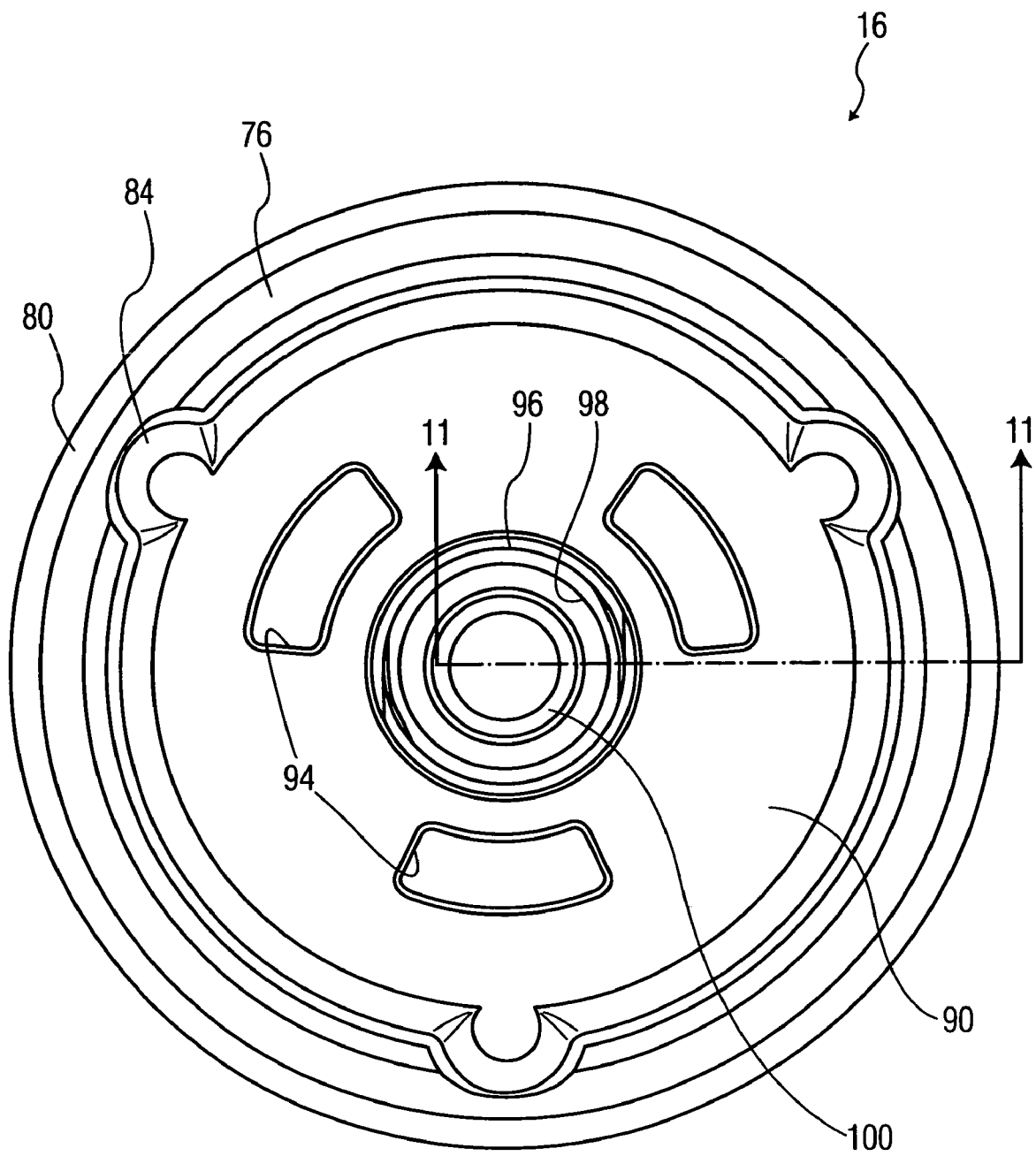
FIG. 10 is a top plan view of the hub.
Figure 11:
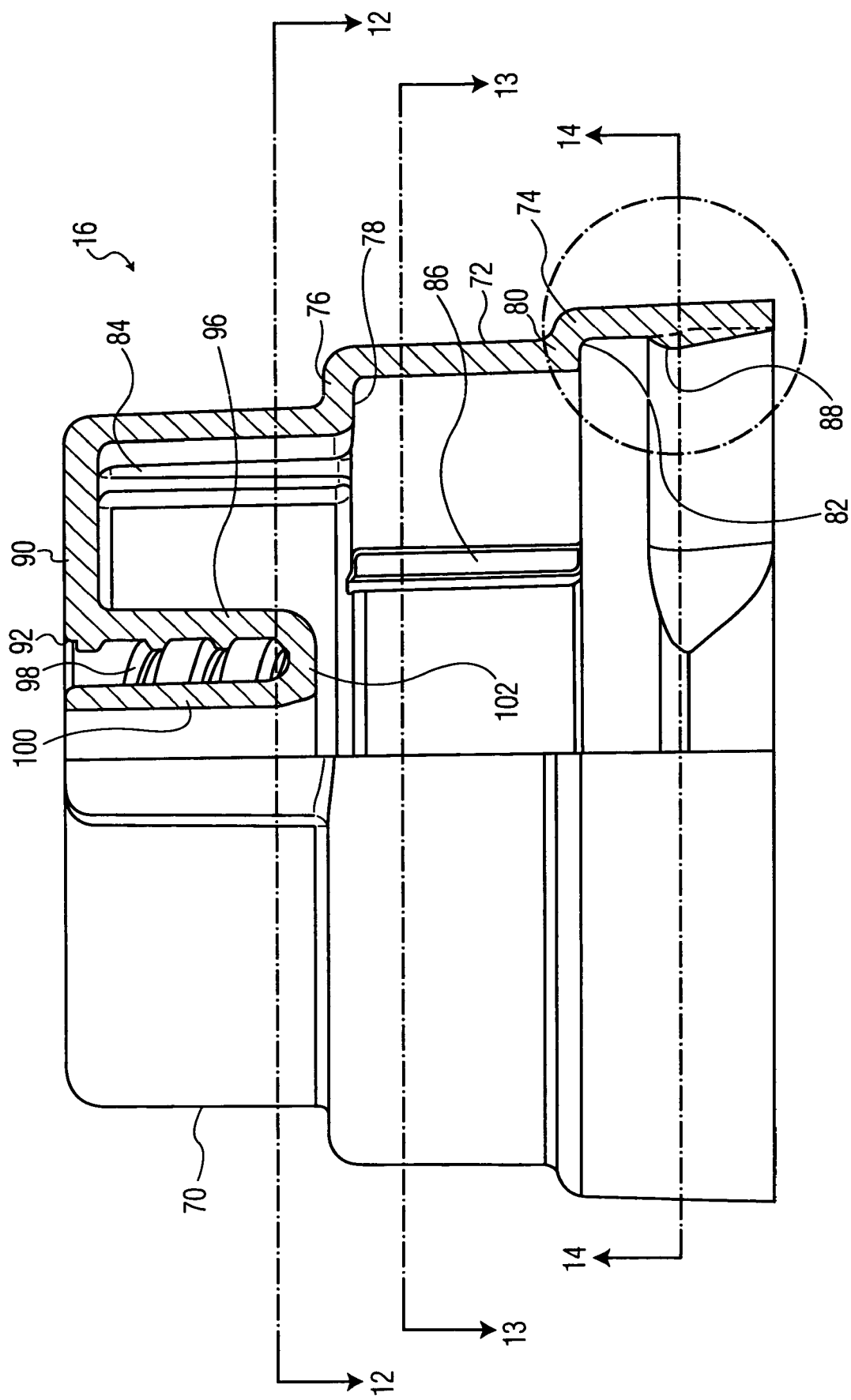
FIG. 11 is a cross-sectional view of the hub, taken along line 11-11 of FIG. 10.
Figure 12:
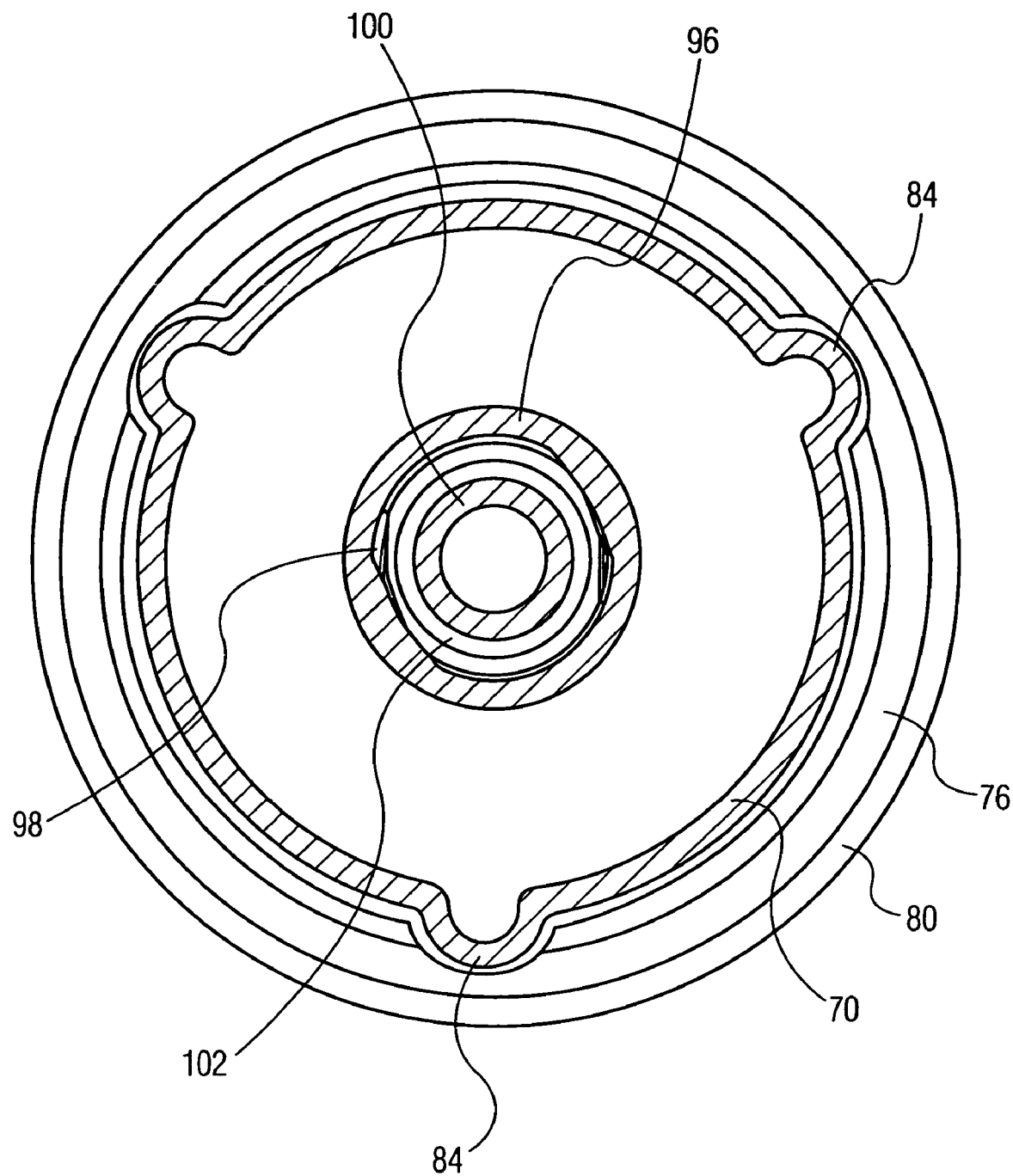
FIG. 12 is a cross-sectional view of the hub, taken along line 12-12 of FIG. 11.
Figure 13:
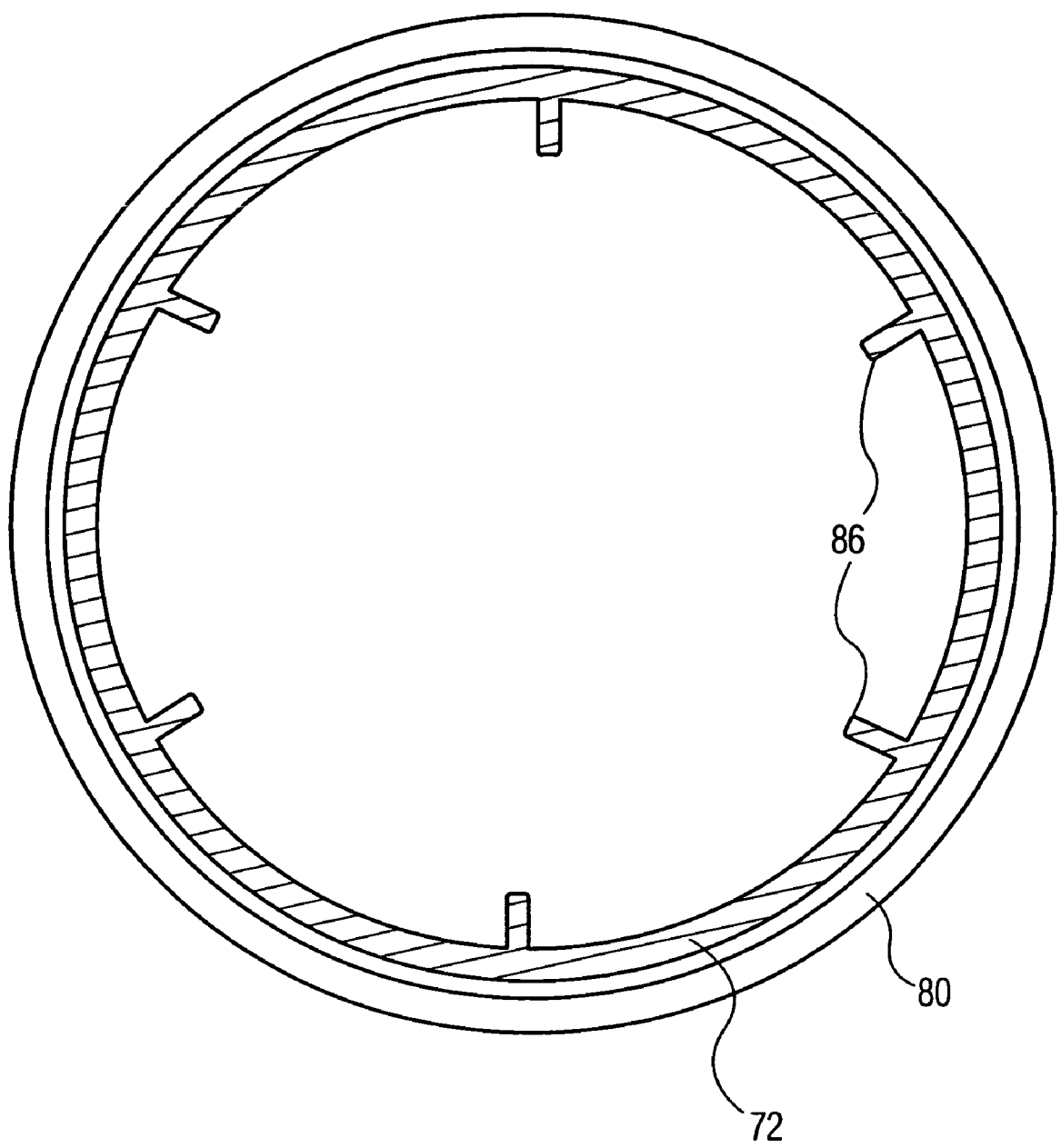
FIG. 13 is a cross-sectional view of the hub, taken along line 13-13 of FIG. 11.
Figure 14:
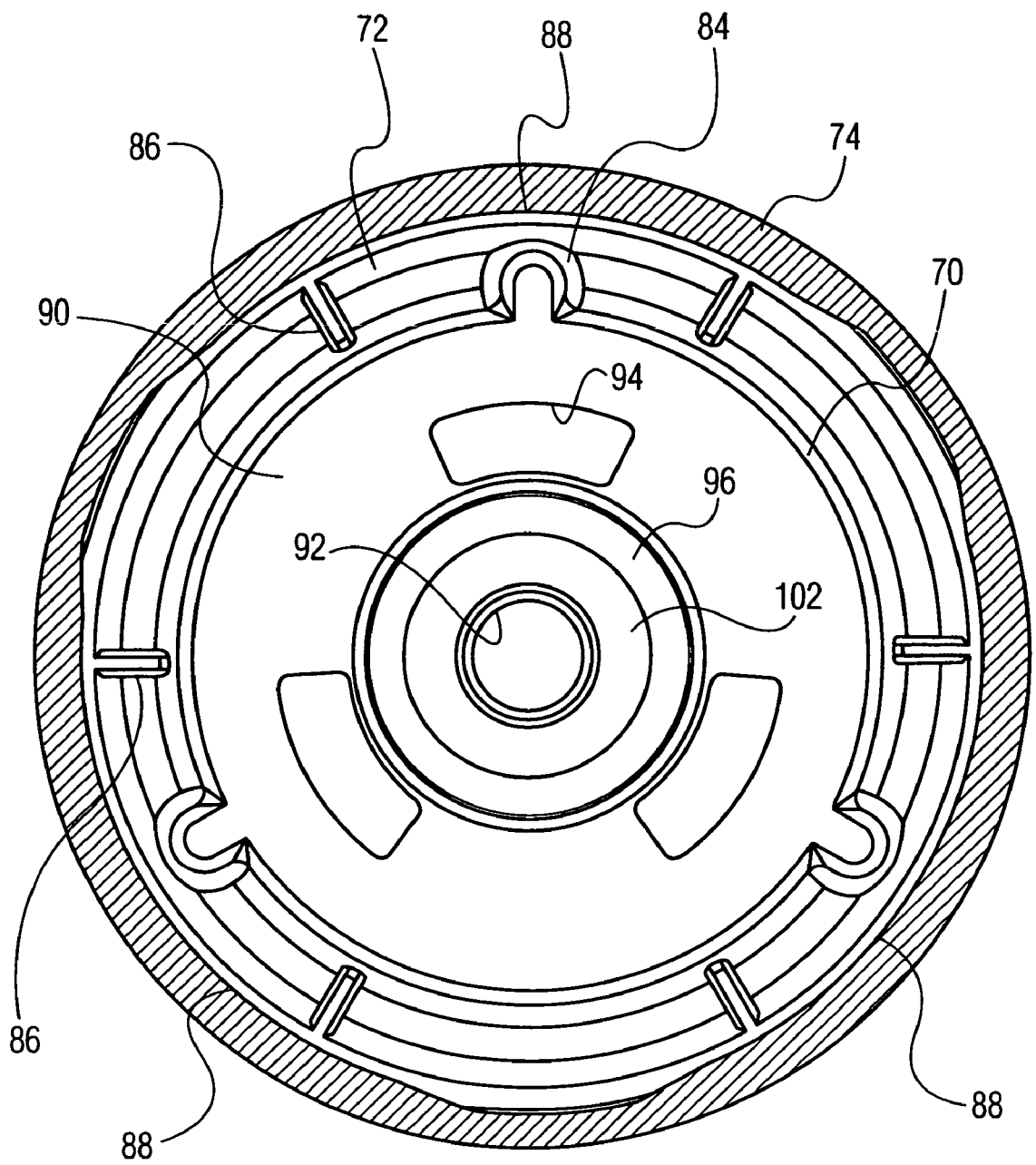
FIG. 14 is a cross-sectional view of the hub, taken along line 14-14 of FIG. 11.
Figure 15:
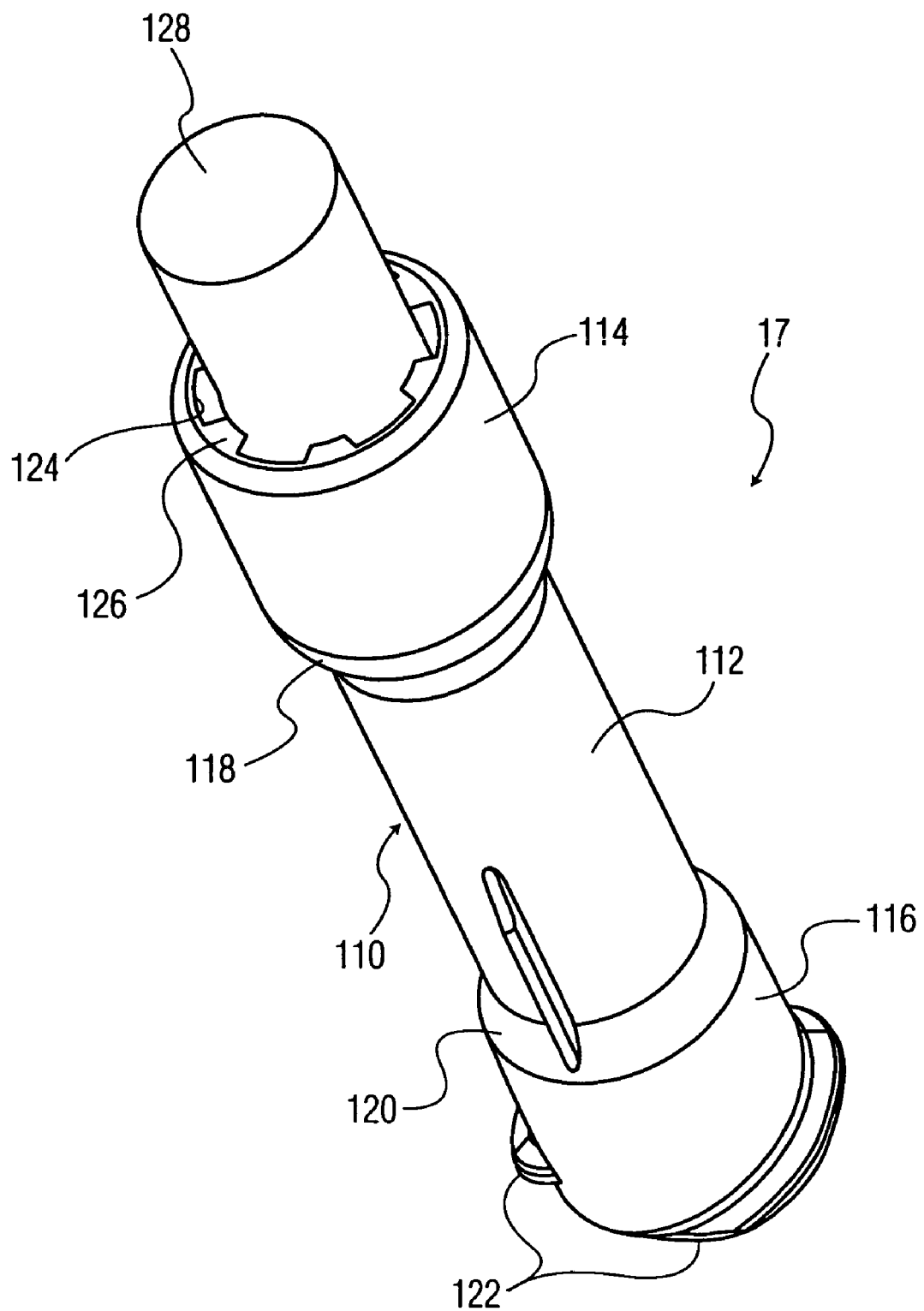
FIG. 15 is a perspective view of the applicator tube.
Figure 16:
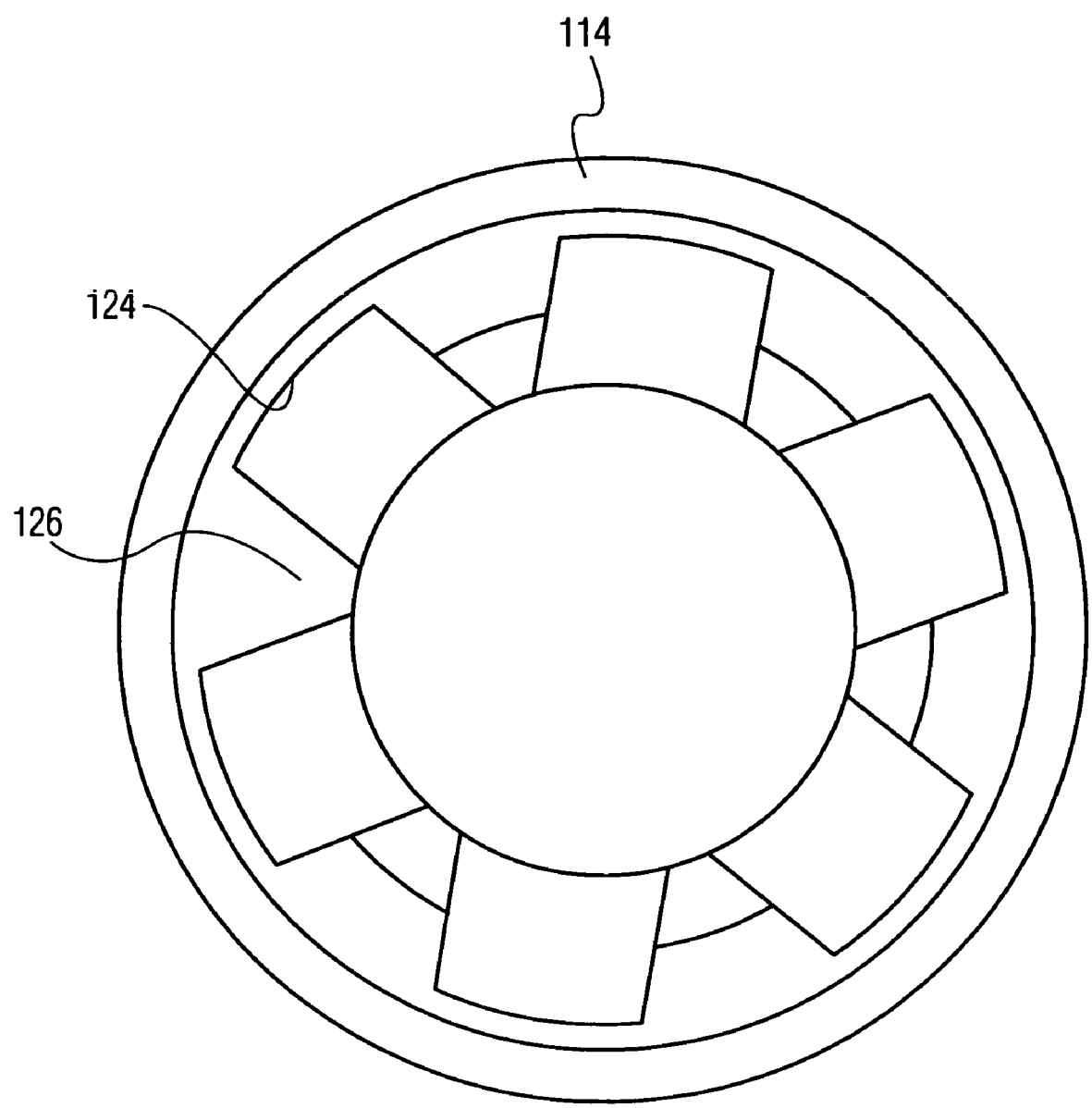
FIG. 16 is a top plan view of the applicator tube.
Figure 17:
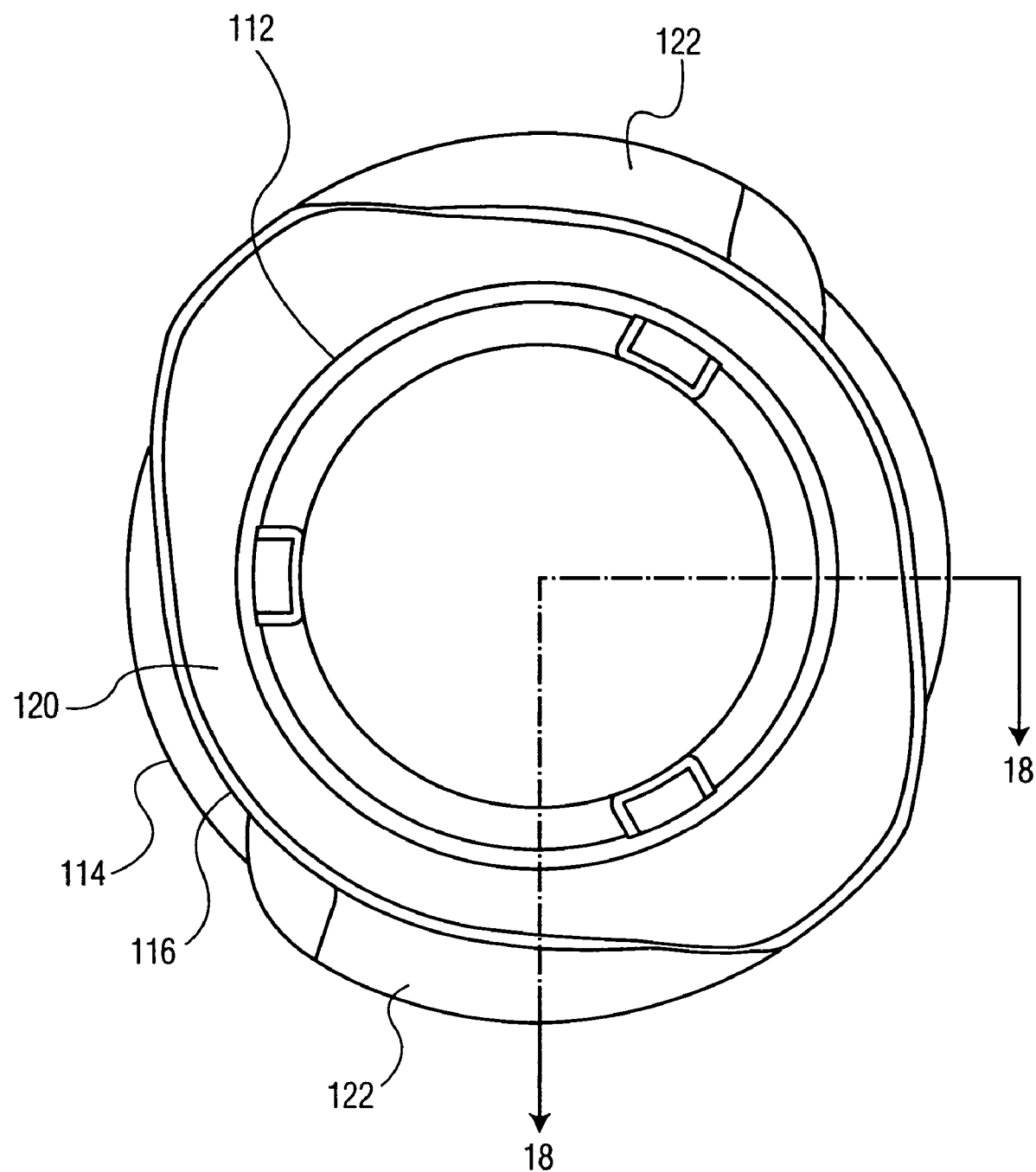
FIG. 17 is a bottom plan view of the applicator tube.
Figure 18:
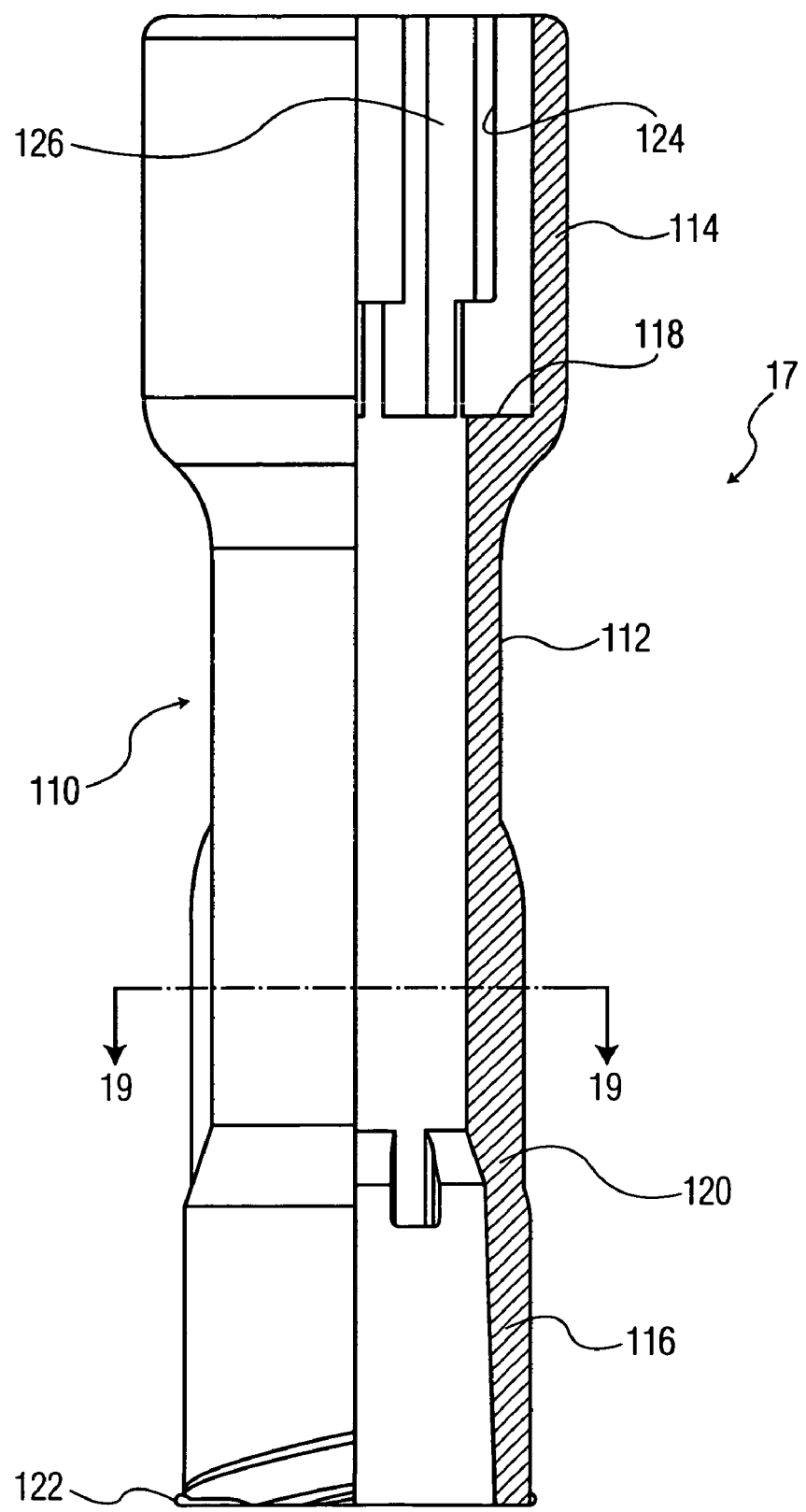
FIG. 18 is a cross-sectional view of the applicator tube, taken along line 18-18 of FIG. 17.
Figure 19:
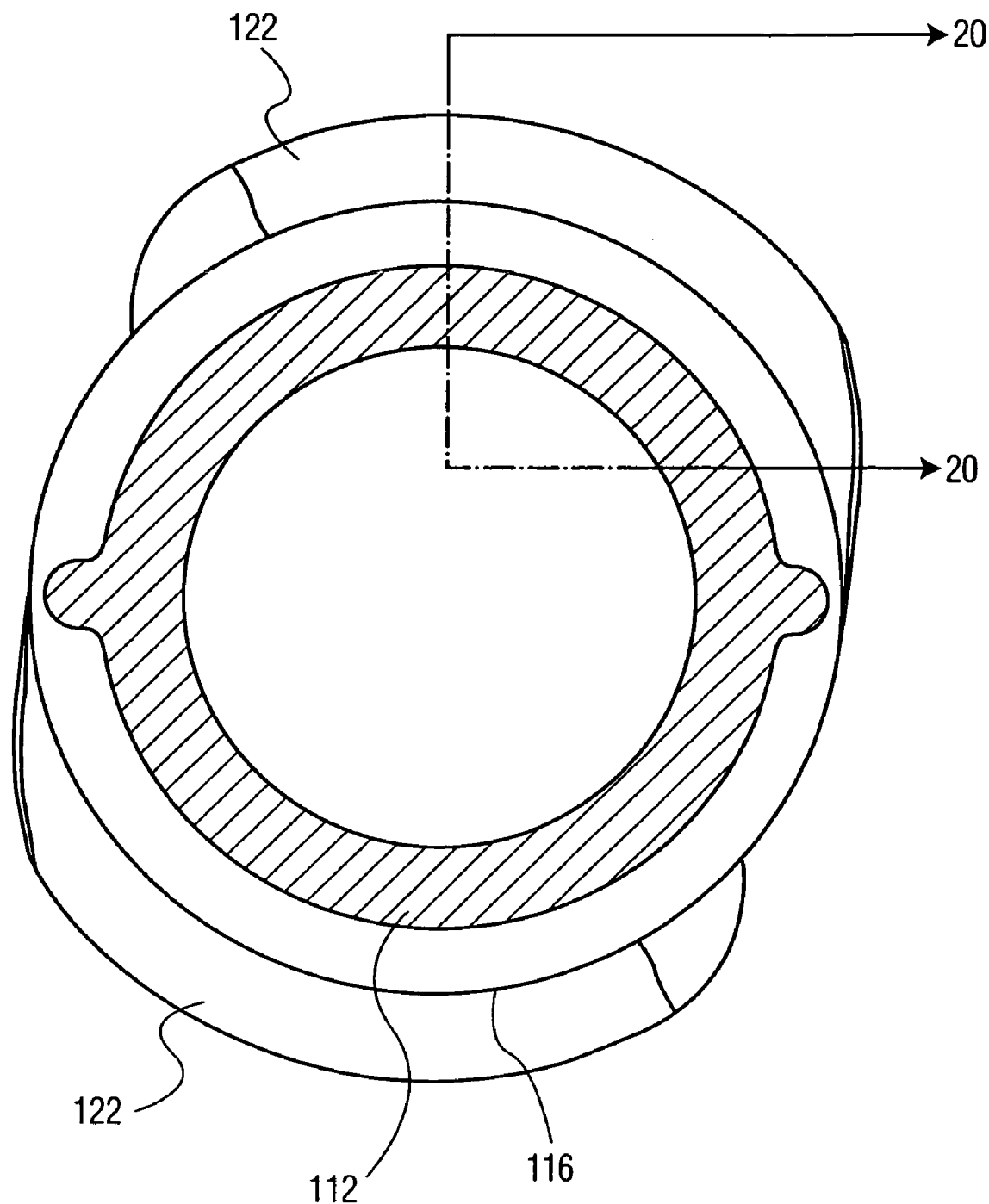
FIG. 19 is a cross-sectional view of the applicator tube, taken along line 19-19 of FIG. 18.
Figure 20:
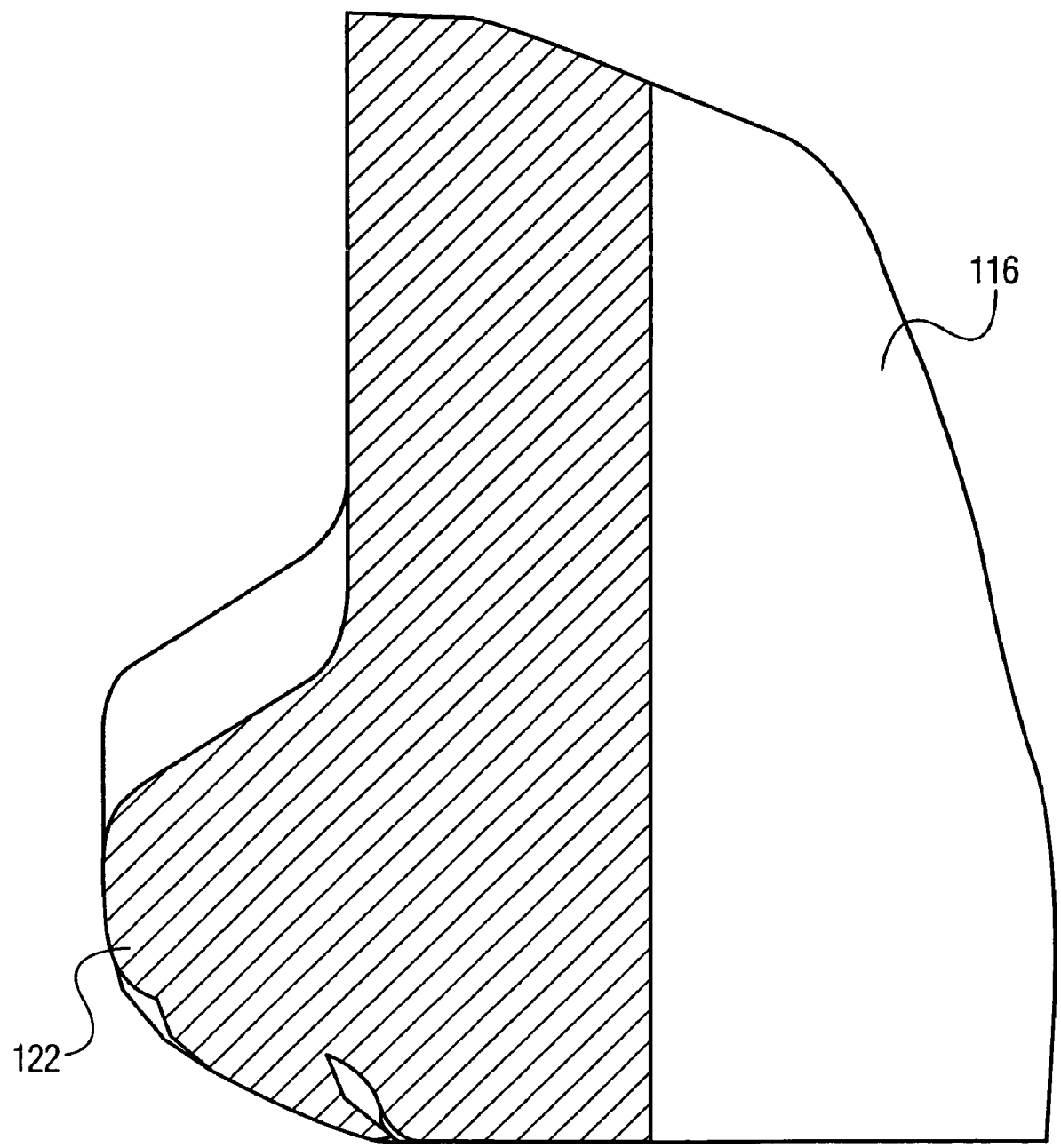
FIG. 20 is a cross-sectional view of the applicator tube, taken along line 20-20 of FIG. 19.
Figure 21:
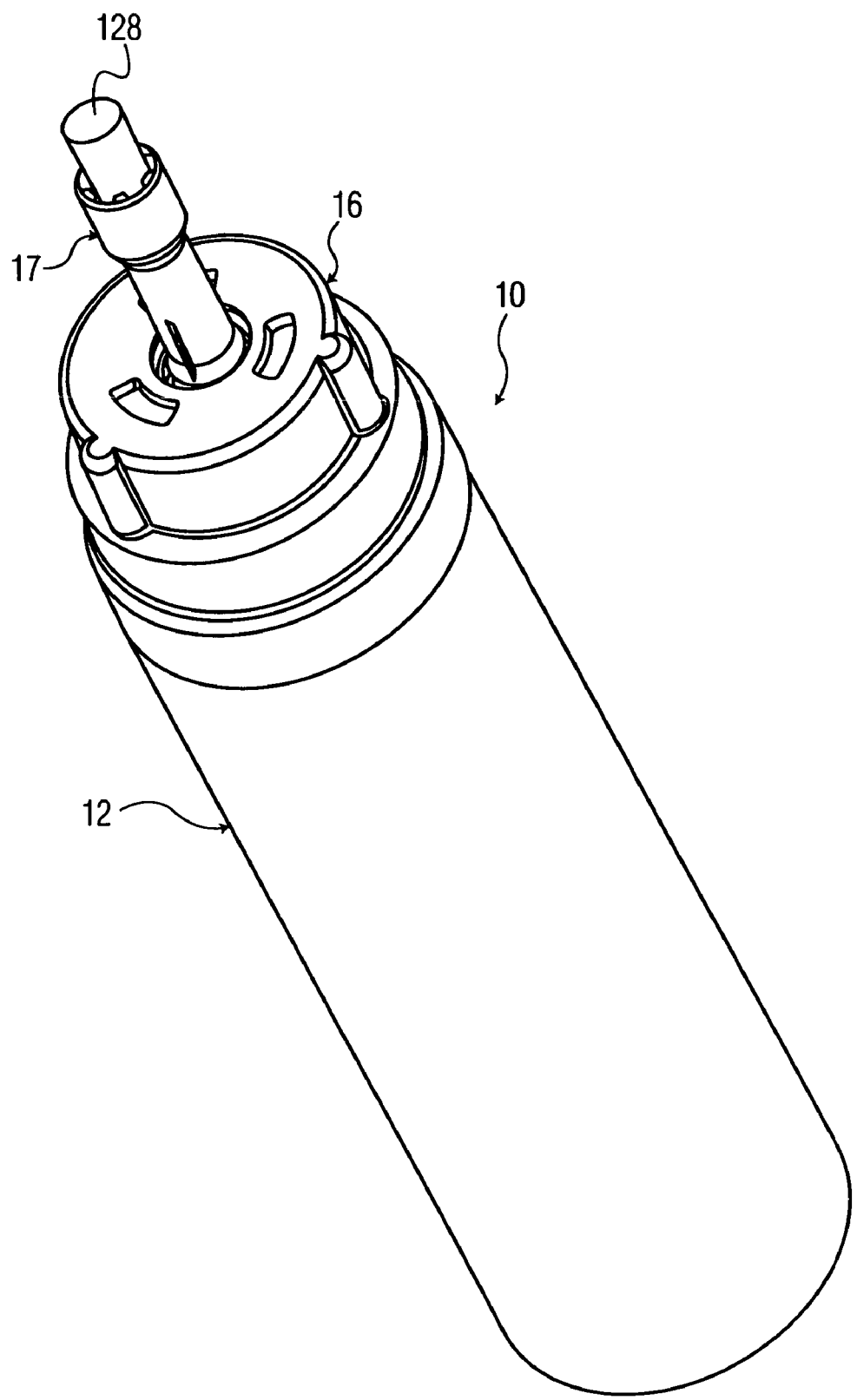
FIG. 21 is an assembled perspective view similar to FIG. 1, showing the applicator tube assembled with the hub which is mounted on the propellant container.
Figure 22:
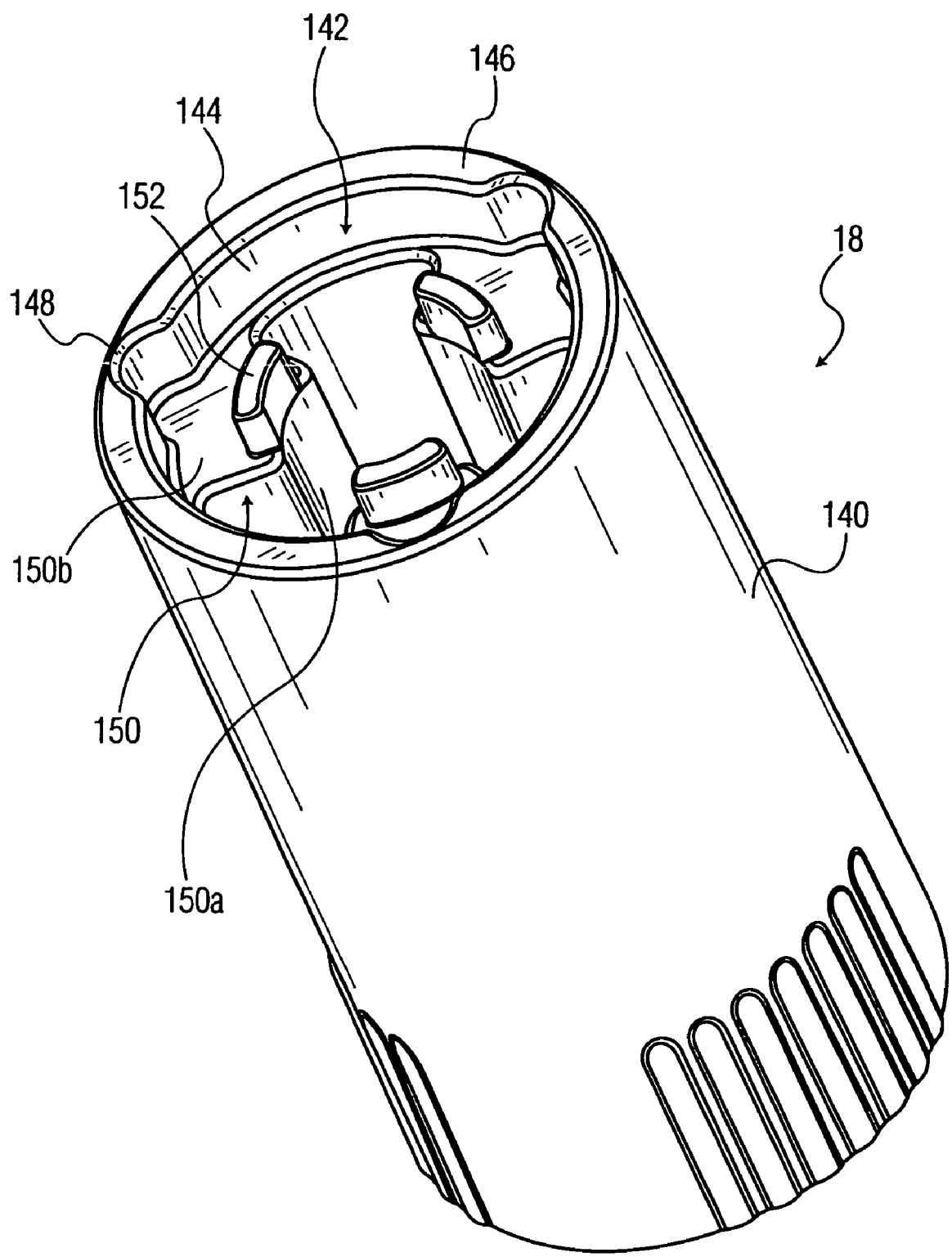
FIG. 22 is a perspective view of the mounting base.
Figure 23:
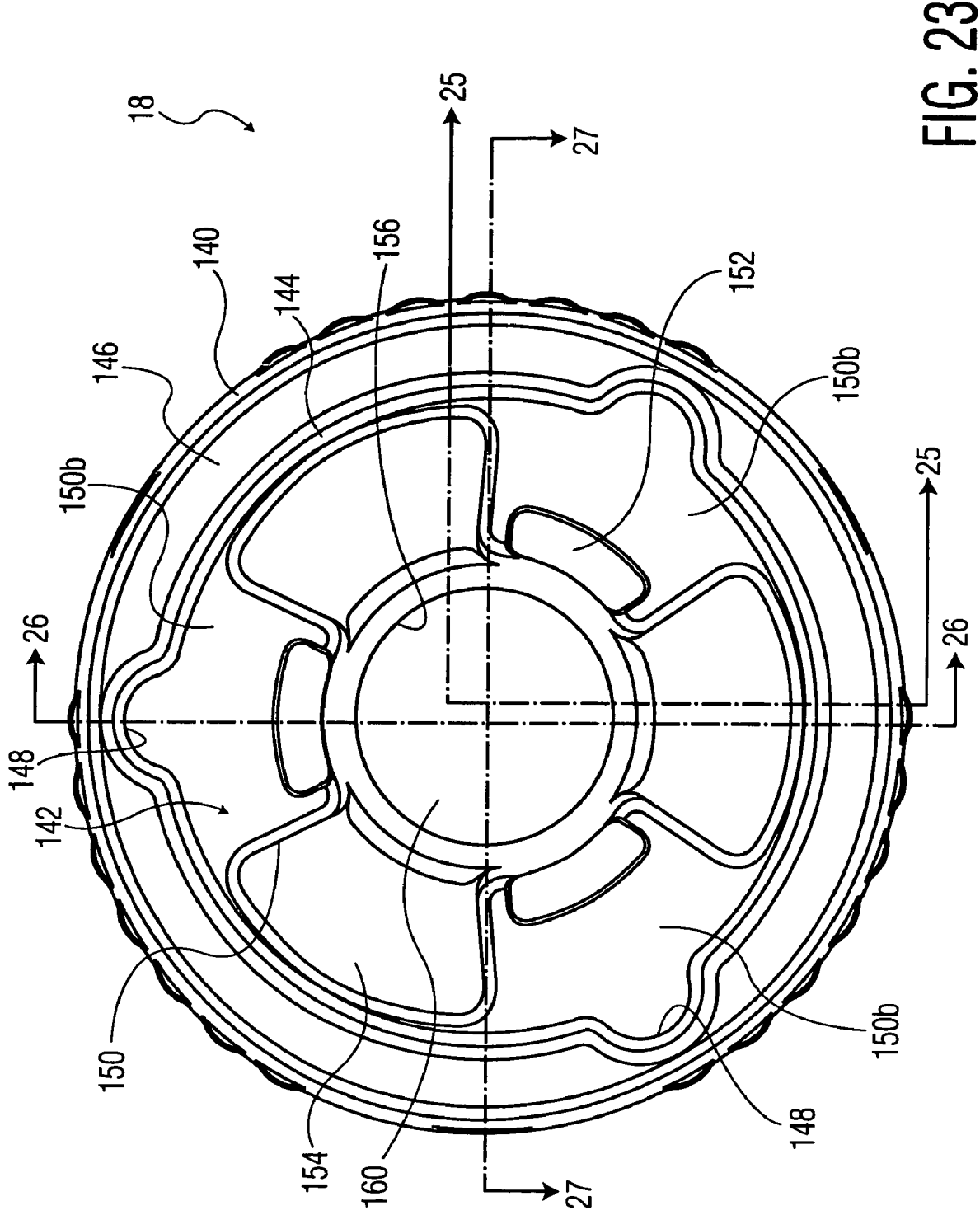
FIG. 23 is a top plan view of the mounting base.
Figure 24:
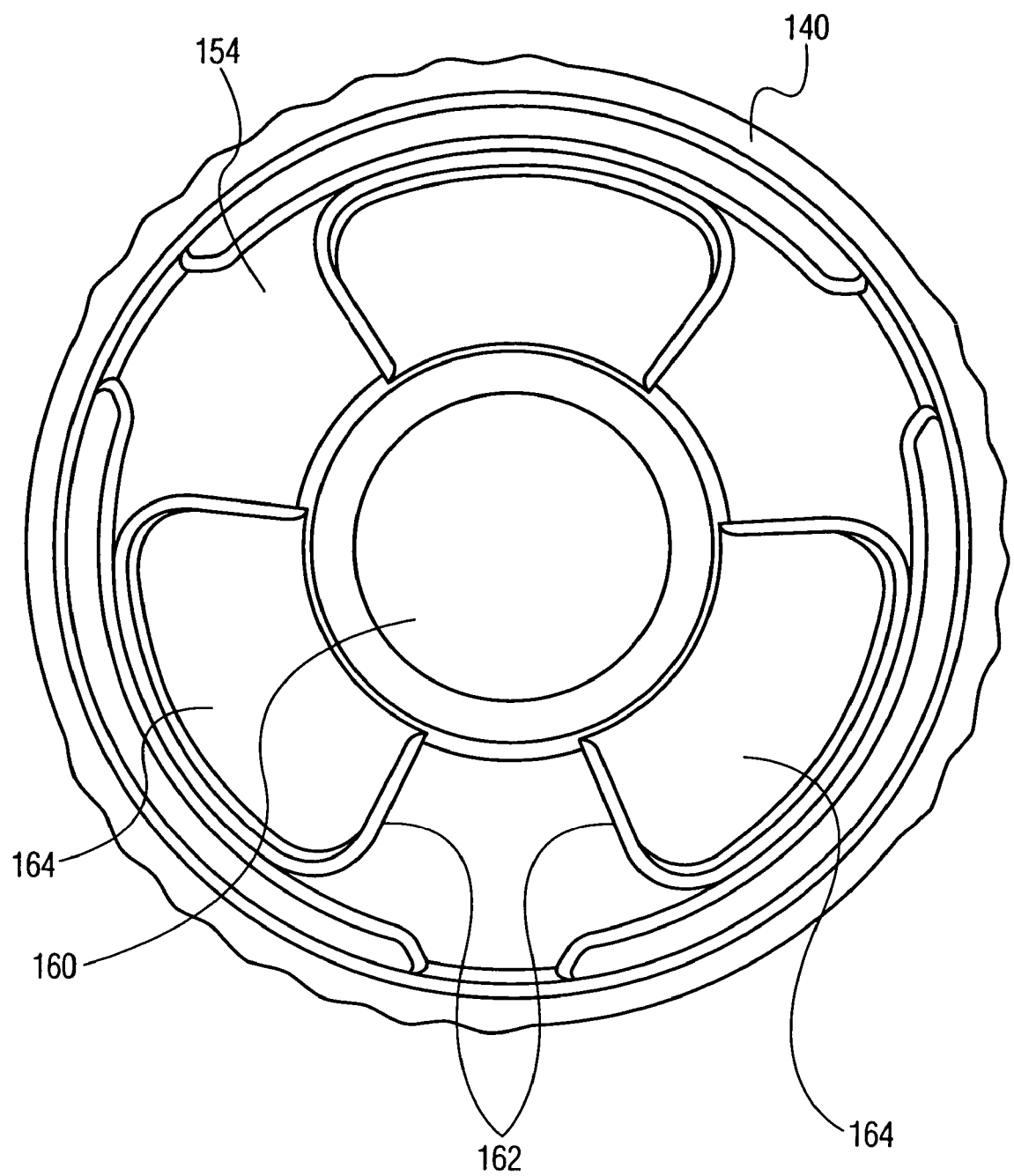
FIG. 24 is a bottom plan view of the mounting base.
Figure 25:
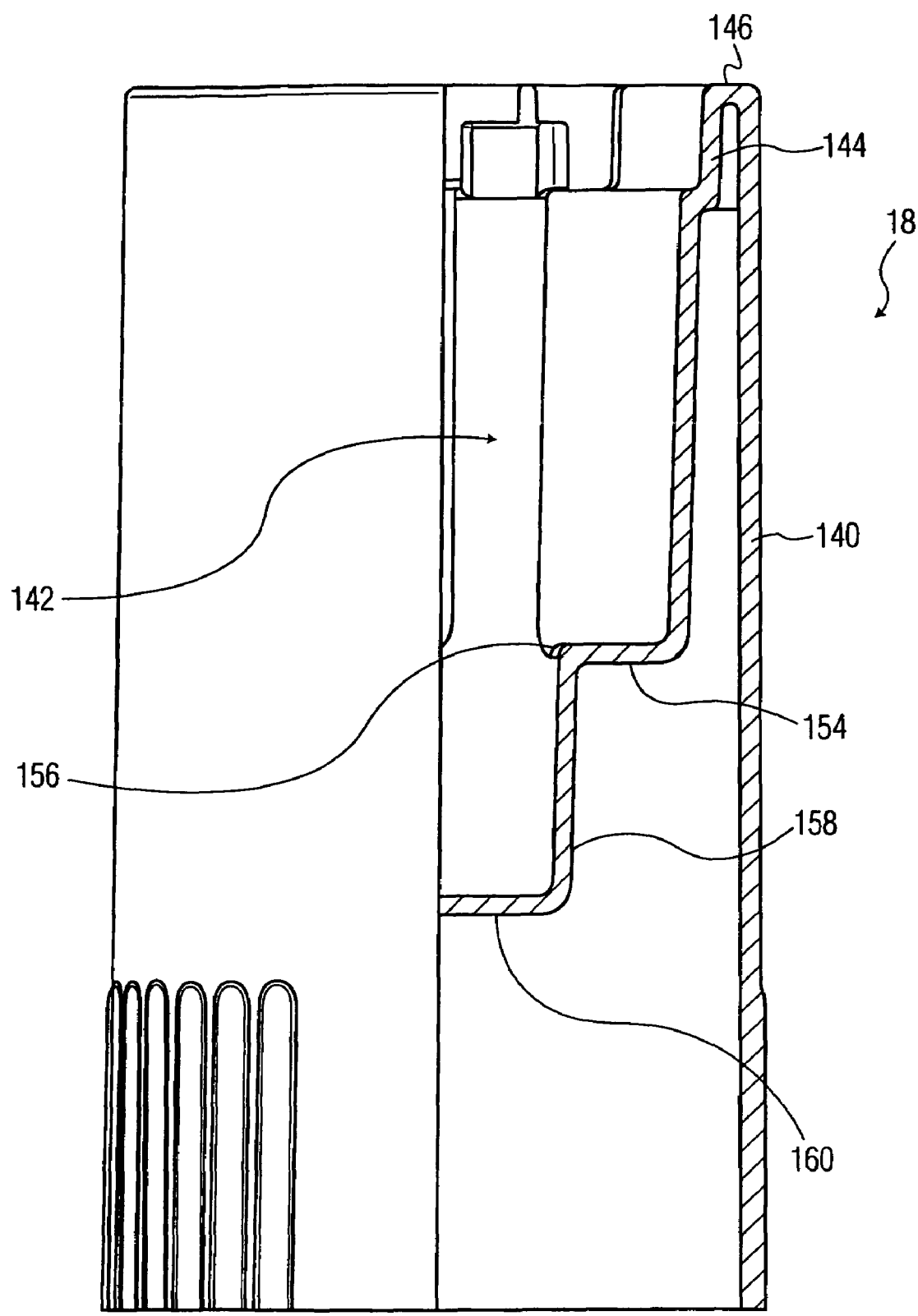
FIG. 25 is cross-sectional view of the mounting base, taken along line 25-25 of FIG. 23.
Figure 26:
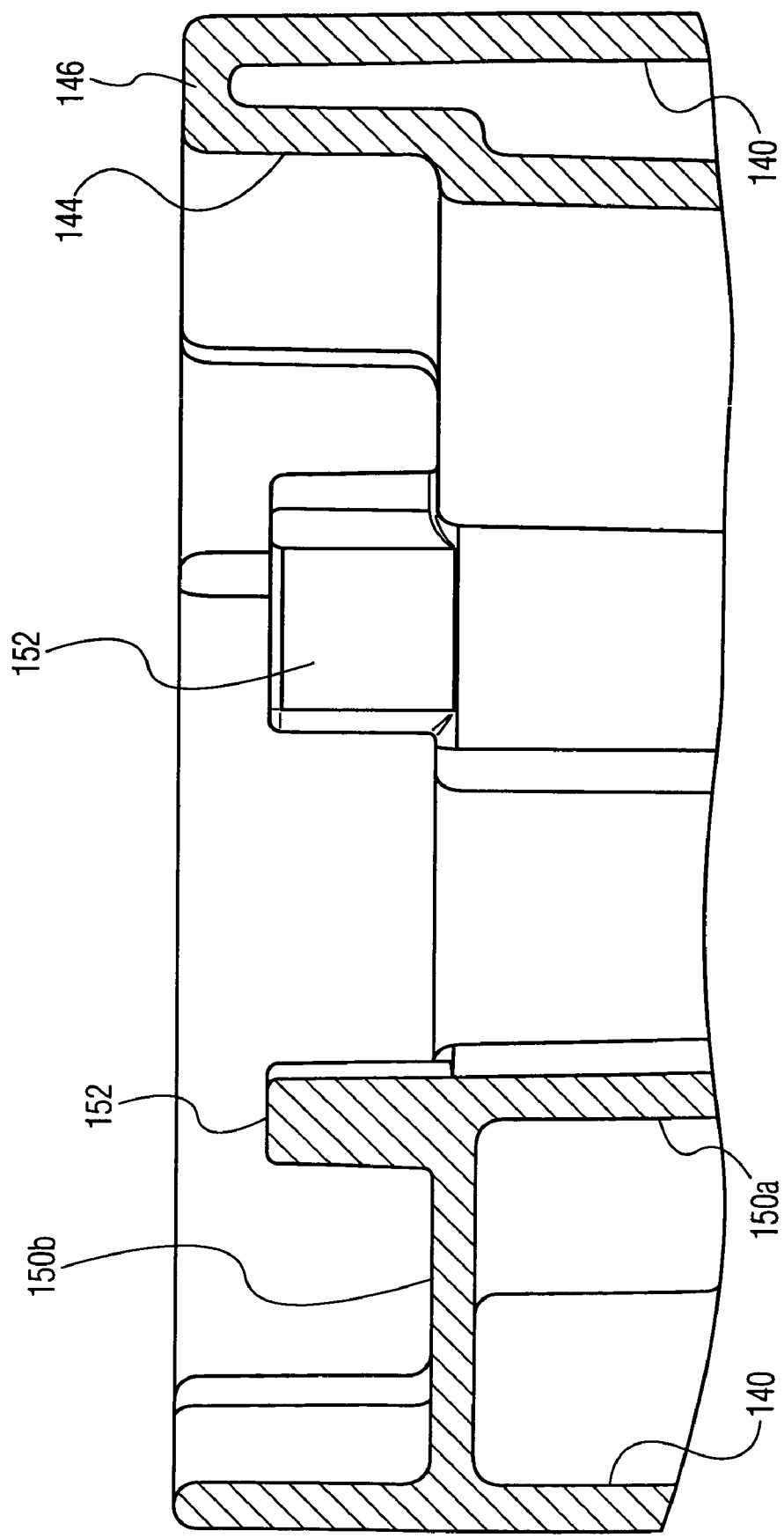
FIG. 26 is cross-sectional view of the mounting base, taken along line 26-26 of FIG. 23.
Figure 27:
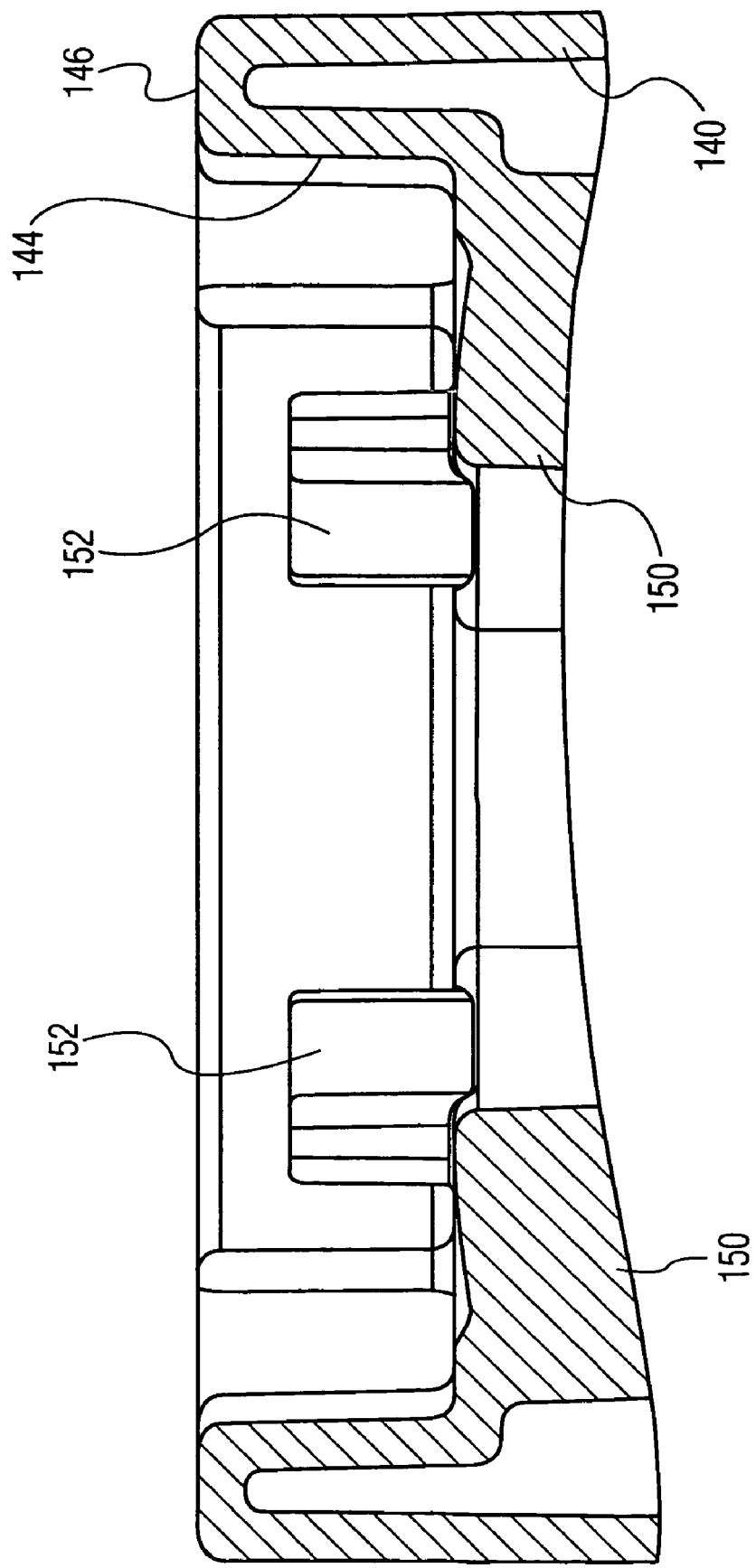
FIG. 27 is cross-sectional view of the mounting base, taken along line 27-27 of FIG. 23.

Referring to the drawings, and initially to FIGS. 1 and 2, a cryosurgery device 10 according to the present invention includes a propellant container 12 which holds a liquid refrigerant, an actuation cup 14 positioned on the stem of propellant container 12, a hub 16 mounted over actuation cup 14 and press fit onto propellant container 12, an applicator tube 17 secured to hub 16 and a mounting base 18 for providing actuation to supply the refrigerant to applicator tube 17. The device is adapted for use to remove various skin lesions, including verruca (warts), keratoses, achrocordon, molluscum contagiosum, age spots, dermatofibroma, keloids, granuloma annulare, porokeratosis plantaris, angiomas, lentigo maligna, keratocanthoma, basal cell, Bowen's disease, lentigo discreta, chondrodermatitis, epithelial nevus, leokoplakia, granuloma pyogenicum, and Kaposi's sarcoma. However, for the sake of brevity, the following description will refer only to treatment of verruca; treatments for the other conditions are similar, except that the sizes of the applicator tips and the duration of contact with the lesions can vary.

As shown in FIGS. 1 and 2, propellant container 12 includes an annular side wall 20, a bottom wall 22 which closes the lower end of annular side wall 20, a top wall 24 which closes the upper end of annular side wall 20. A reduced diameter neck 26 is provided centrally in top wall 24 and extends upwardly therefrom. Neck 20 has a top wall 28 that partially closes the upper end thereof and which includes a central opening 30 that is in open fluid communication with the interior of container 12 for delivering a liquid refrigerant held in container 12. As is typical in the art, aerosol containers may be formed from plated steel, aluminum, and other materials; the choice of material is not particularly critical, resistance to corrosion from contact with the contents and an ability to withstand the internal pressures that are generated being the more important considerations.

The liquid refrigerant can be any suitable liquid refrigerant for use as a cryogenic agent to reduce the temperature of wart tissue to a temperature to freeze the skin, such that permanent, irreversible rupture of cellular membranes of cells of the skin lesion occurs while the cryogenic agent is evaporating. If the temperature of a wart is lowered below about −20° C. for at least about twenty seconds, the wart tissue will be destroyed. Many low-boiling refrigerant/aerosol propellant materials are suitable for this purpose, including halogenated hydrocarbons, ethers, and hydrocarbons. For environmental reasons, the formerly very common chlorofluorocarbon refrigerants have been prohibited for most uses, generally being replaced by fluorohydrocarbon compounds; for example, the commercial refrigerant 1,1,1,2-Tetrafluoroethane, which has a boiling point of −26.5° C., is useful in the present invention. The materials may be mixtures of refrigerant compounds to lower the container internal pressures, to achieve a desired boiling point, or for other reasons. Those skilled in the art are aware of numerous useful refrigerant compounds and mixtures.

Examples of useful mixtures are: 82 weight percent dimethyl ether and 18 weight percent propane; and 95 weight percent dimethyl ether, 2 weight percent propane, and 3 weight percent isobutane. For purposes of the present invention, a very suitable liquid refrigerant is a mixture of 75 weight percent dimethyl ether and 25 weight percent propane, which produces temperatures below about −30° C. on the surface of skin of a person when applied using the following described device.

A conventional spring-loaded pressurized "continuous" aerosol valve 32 is provided in reduced diameter neck 26 of container 12. The construction details of valve 32 are well known and the specific construction of valve 32 does not form part of the present invention. Examples of such valves can be found throughout the patent literature, for example, in U.S. Pat. Nos. 6,039,306; 6,318,603; and many other patents; as well as in A. R. Gennaro, Ed., *Remington: The Science and Practice of Pharmacy*, 20$^{th}$ Ed., Lippincott, Williams & Wilkins, Baltimore, Md., 2000, pages 971-972; the entire disclosures of which are incorporated herein by reference. In the embodiment shown, dip tube 34 is connected with valve 32 and extends into container 12, and a short outlet stem 36 extends out of container 12. Although not depicted in the figures, it will be appreciated that valve 32 further comprises a vapor tap that is used to expel gases along with the liquid expelled through a dip tube 34 to preferably form a mist when the valve is used in the up-right position. However, in a preferred embodiment discussed throughout this specification, container 12 is placed in contact with base 18 in an inverted position to release the cryogen liquid, which eliminates the effectiveness of dip tube 34 as it extends above the level of liquid in container 12 as inverted. Thus, in this embodiment, dip tube 34 can be made to extend into the interior of container 12 for only a very short distance or, alternatively, the dip tube can even be eliminated, so that liquid refrigerant will be delivered exclusively through the vapor tap when container 12 is inverted.

In addition, an annular lip 38 extends upwardly from the upper outer edge of annular wall 20, and includes an annular undercut 40, the purpose for which will become apparent from the discussion hereafter.

Referring now to FIGS. 1-8, actuation cup 14 includes a main body having a generally annular outer wall 50 which is partially closed at its lower end by a bottom wall 52 having a central opening 54 with a first inner diameter. Annular outer wall 50 is open at its upper end 56, and an annular ledge 57 extends outwardly from the upper end 56 in a radial direction, forming an upper annular actuating surface 58 thereat. An outlet tube 60 of the same first inner diameter extends upwardly from bottom wall 52 and is coaxial with and in fluid communication with central opening 54. Outlet tube 60 preferably extends to a height just above upper annular actuating surface 58, although the present invention is not limited thereto. An inlet tube 62 having a second inner diameter which is greater than the first inner diameter of outlet tube 60 extends downwardly from the lower surface of bottom wall 52, and is in fluid communication with outlet tube 60 through central opening 54. Because of the larger inner diameter of inlet tube 62, an inner annular shoulder 64 is formed at the lower surface of bottom wall 52 in surrounding relation to central opening 54 and encased by inlet tube 62. Actuation cup 14 sits on short outlet stem 36 such that short outlet stem 36 is received in outlet tube 60, with the upper edge of short outlet stem 36 seating at inner annular shoulder 64.

Thus, as a result of pressure applied to upper annular actuating surface 58 of actuation cup 14, inner annular shoulder 64 forces short outlet stem 36 inwardly of container 12 in order to open valve 32 and release the refrigerant, which then travels from short outlet stem 36, through outlet tube 60. In order to reinforce annular outer wall 50 as a result of such pressure without adding substantially to the material and costs of actuation cup 14, strengthening ribs 66 extend out radially from the outer surface of annular outer wall 50, in angularly spaced relation from each other, and are also connected to the underside of annular ledge 57.

As discussed above, a hub 16 is mounted over actuation cup 14 and is press fit onto propellant container 12. Referring now to FIGS. 1, 2 and 9-14, hub 16 includes an upper annular side wall 70 having a first diameter, a middle annular side wall 72 of a second larger diameter, and a lower annular side wall 74 of a third largest diameter. A radially directed annular wall 76 connects the lower edge of upper annular side wall 70 to the upper edge of middle annular side wall 72 to form an inner annular shoulder 78 thereat, and a radially directed annular wall 80 connects the lower edge of middle annular side wall 72 to the upper edge of lower annular side wall 76 to form an inner annular shoulder 82 thereat. Further, the material of upper annular side wall 70 is pushed out at three equiangularly spaced vertical locations to form three equiangularly spaced aligning ribs 84 for alignment purposes as will be understood from the discussion hereafter. In like manner, six equiangular vertical reinforcing ribs 86 extend inwardly in a radial direction from the inner surface of middle annular side wall 72.

Hub 16 is open at the lower end of lower annular side wall 74, and has three equiangularly spaced snap-in beads 88 on the inner surface thereof. As a result, hub 16 can be snap fit onto propellant container 12. In such case, annular snap-in beads 88 will snap over annular undercut 40 in order to hold hub 16 on container 12.

A top wall 90 closes the upper edge of upper annular side wall 70 and includes a central opening 92, as well as three equiangularly spaced, slightly arcuate slots 94 in surrounding relation to central opening 92. When hub 16 is snapped onto container 12, as shown best in FIG. 2, upper annular actuating surface 58 of actuator cup 14 is positioned against or very close to the lower surface of top wall 90, with upper annular actuating surface 58 immediately below slots 94.

An annular boss 96 extends down from the lower surface of top wall 90 in surrounding relation to central opening 92 for a distance almost to the lower edge of upper annular side wall 70. The inner surface of annular boss 96 is formed with a helical screw thread 98. A hollow shaft 100 having an outer diameter less than the inner diameter of annular boss 96, is provided coaxially within annular boss 96 and is of substantially the same height as annular boss 96. The lower edges of annular boss 96 and hollow shaft 100 are connected together by an annular connecting wall 102. This latter arrangement is provided to capture and hold applicator tube 17 therein.

As discussed above, applicator tube 17 is secured to hub 16. As shown in FIGS. 15-21, applicator tube 17 has a barbell-like shape. Specifically, applicator tube 17 is formed by a unitary hollow shaft 110 of a generally constant thickness throughout. Hollow shaft 110 includes a center section 112 of a first diameter, an upper section 114 of a diameter which is greater than the first diameter of center section 112 and a lower section 116 of a diameter which is also greater than the first diameter of center section 112. An annular shoulder 118 is formed at the connection of the lower end of upper section 114 with the upper end of center section 112, while a second annular shoulder 120 is formed at the connection of the upper end of lower section 116 with the lower end of center section 112.

Two diametrically opposite projections 122 extend outwardly in the radial direction from the outer surface of lower section 116 at the lower edge thereof. The outer diameter of lower section 116 is less than the inner diameter of annular boss 96 while the inner diameter of lower section 116 is greater than the outer diameter of hollow shaft 100 so as to fit therebetween. In this manner, when the lower end of lower section 116 is inserted between boss 96 and hollow shaft 100, and then rotated, projections 122 engage with helical screw thread 98 to releasably lock applicator tube 17 to hub 16, as shown best in FIG. 21.

The inner surface of upper section 114 is provided with equiangularly spaced grooves 124 that extend vertically and in the radial direction, so as to define a plurality of equiangularly spaced vertical projections 126 extending inwardly in the radial direction. The grooves 124 serve to conduct the refrigerant from outlet tube 60 through applicator tube 17 into contact with cylindrical tip 128.

Cylindrical tip 128 formed from a porous material is friction fit in upper section 114 and held therein by projections 126. After contact with refrigerant, tip 128 is used to freeze the skin. Tip 128 can be made of any suitable material, such as a polymeric foam, a sintered thermoplastic, a sintered metal, a glass or ceramic frit, or a polyolefin or polyester nonwoven fabric. Preferably, tip 128 is secured to applicator tube 17, for example by thermal welding, ultrasonic welding, an adhesive, etc. In general, the void volume of the porous material should be greater than about 50 percent to provide sufficient capacity for receiving liquid refrigerant for a period of time sufficient to chill tip 128 to a therapeutically effective temperature. A maximum void volume will typically not exceed about 90 percent, and will depend on the relative rigidity and strength of the material of construction so that the tip will retain its general shape during use.

Preferably, tip 128 comprises a nonwoven material in which oriented bicomponent polyethylene/polyester fibers are thermally bonded into a rod configuration, having a density about 0.2 g/cm$^3$ and a void volume about 80 percent. The tip can be shaped as desired, such as cylindrical, conical pointed, truncated conical, or other shapes that provide a desired skin contact area. An advantage of nonwoven material is its rigidity, so that the desired shape is generally maintained during use, while also providing a good degree of comfort by being somewhat deformable while held in contact with the skin. Also, the important properties of nonwoven materials are not substantially changed as the temperatures vary during use in the invention.

In a presently preferred embodiment, an applicator tube 17 is about 25 mm (1 inch) in length and center section 112 has an inner diameter about 5 mm (0.2 inches); the inner diameter of upper section 114, between opposite projections 126, is about 6 mm (0.23 inches) to enhance retention of the porous tip. The porous tip has a diameter about 6.4 mm (0.25 inches) and a length about 12.7 mm (0.5 inches); at least about half of the length of the tip will typically extend beyond the upper edge of the applicator tube. When formed from the nonwoven material described above, a tip of these dimensions will have a mass about 75 mg.

When valve 32 is opened, the liquid refrigerant flows through applicator tube 17 via grooves 124 and contacts tip 128, thereby chillng tip 128 by the immediate evaporation of refrigerant. Then, chilled tip 128 can be briefly pressed against a wart to be removed from the skin. As refrigerant evaporates from the tip, it may be replenished during at least a portion of the treatment time by liquid remaining in the tube. Preferably, for hygienic reasons, the applicator tube 17 and tip 128 are used only once, and then will be discarded.

In order to contain the refrigerant while valve 32 is open to chill tip 128 base 18 is provided. Specifically, as shown in FIGS. 1 and 22-27, base 18 includes a cylindrical outer shell 140 and an inner actuating assembly 142 mounted to and within outer shell 140. Specifically, inner actuating assembly 142 includes three equiangularly spaced short arcuate walls 144 extending vertically down within outer shell 140, with the upper edges of short arcuate walls 144 connected to the upper edge of outer shell 140 by connecting walls 146. As a result, aligning gaps or recesses 148 are formed between side edges of short arcuate walls 144.

Three equiangularly spaced, inwardly extending projections 150 are connected to outer shell 140 immediately below gaps or recesses 148. Each projection 150 has a generally trapezoidal shape with the inner surface 150*a* thereof being generally arcuate. Each projection 150 extends down to a distance to an approximate mid-point of the length of outer shell 140. An upstanding arcuate key 152 extends upwardly from the upper surface 150*b* of each projection 150 and is positioned near inner surface 150*a*, the purpose for which will become apparent from the discussion hereafter.

The "lock and key" combination of keys 152 and slots 94 acts to prevent opening of the valve unless base 18 is properly in place over hub 16. Thus, the release of refrigerant will take place into an enclosed space, and the user will be protected against a potentially injurious contact with the refrigerant. There typically will be up to about six each of keys 152 and slots 94, and their shapes can vary from the particular embodiment shown, such as being round, square, rectangular, etc. Preferably there will be at least two of the keys and slots. To provide additional security against injury from misuse, the device is designed to deliver refrigerant in liquid form only when container 12 is inverted, and the slots 94 are less accessible to a user. Excess amounts of refrigerant will be contained within the central opening of the base, which central opening is closed by bottom wall 160.

The lower edges of projections 150 are closed by an annular wall 154 at a substantial mid-point of the length of outer shell 140, with annular wall 154 defining a central opening 156 therein. A cylindrical wall 158 extends down from annular wall 154 in surrounding relation to central opening 156, and is closed at its lower end by a bottom wall 160. Trapezoidal projections 162 of a similar shape to projections 150 are formed on the outer surface of cylindrical wall 158 and are secured to the lower surface of annular wall 154 in alignment with the spaces between projections 150, in order to add structural rigidity to cylindrical wall 158. The lower ends of trapezoidal projections 162 are closed by lower walls 164.

In operation, actuator cup 14 and hub 16 are preferably pre-assembled with propellant container 12. Then, applicator tube 17 is assembled with hub 16 by the user by inserting the lower end of lower section 116 between boss 96 and hollow shaft 100, and then rotating applicator tube 17, whereby projections 122 engage with helical screw thread 98 to lock applicator tube 17 to hub 16, as shown best in FIG. 21. As discussed above, tip 128 is preferably permanently secured to applicator tube 17. Thereafter, with base 18 positioned on a stable surface, propellant container 12 is inverted and positioned within base 18. In this position, aligning ribs 84 are aligned with and inserted within aligning recesses 148 in order to angularly align container 12 with base 18. Further, applicator tube 17 extends centrally therethrough, with tip 128 being positioned within cylindrical wall 158. Upper surfaces 150b define a limit as to the extent to which hub 16 can be inserted into base 18.

Due to this alignment, keys 152 extend into arcuate slots 94, and upon pressure on container 12, keys 152 engage upper annular actuating surface 58 of actuation cup 14 to push actuation cup 14 inwards toward container 12. As a result of this pressure applied to upper annular actuating surface 58 of actuation cup 14, inner annular shoulder 64 forces short outlet stem 36 inwardly toward container 12 in order to open valve 32 and release the refrigerant, which then travels from short outlet stem 36, through outlet tube 60 of actuator cup 14 and then through applicator tube 17 via grooves 124 so as to contact and chill tip 128 to a therapeutically effective temperature. This takes only a few seconds, and frequently as little as two seconds.

Thereafter, base 18 is removed and, without removing applicator tube 17 from hub 16, tip 128 with the refrigerant contained therein is immediately applied to the wart for a period of, for example, twenty seconds, in order to freeze the wart. After about five minutes, tip 128 will have sufficiently warmed so that the applicator can be safely removed from the device and the applicator tube/tip assembly can be discarded.

Base 18 can be used as a storage cover for the cryogenic surgery device, if the end opposite the end containing keys 152, etc. is sized to provide a friction fit over container 12. An important feature of the device is the containment within base 18 of dispensed liquid refrigerant during the chilling procedure, so that spillage onto the user is unlikely. As a result of this design, it is also contemplated that base 18 can serve as a reservoir for the liquid refrigerant dispensed directly from short outlet stem 36, through outlet tube 60 of actuator cup 14, when applicator tube 17 is not attached to hub 16. In this manner, any known applicator material, such as a metal or nonmetal rod, including polymer materials that can withstand the cryogenic temperatures, can be immersed into the pool of liquid refrigerant for a period of time sufficient to chill the applicator to a therapeutically effective temperature, and then applied to the lesion to be frozen. In equally preferred embodiments, the applicator can comprise the porous tip material described above for tip 128.

With the exceptions of the aerosol container and the tip, all of the device components typically will be molded from one or more thermoplastic materials, such as polyethylene, polypropylene, or other polyolefins and polyolefin copolymers, nylons, polyesters, polyacetals, and polyurethanes. The materials of construction are not critical to the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention as defined by the appended claims.

What is claimed is:

1. A cryosurgery device for use with an aerosol container having a valve and a valve stem extending outwardly from the valve and the container, the container holding a refrigerant therein, the cryosurgery device comprising:

an actuator adapted to seat on a stem of a container in order to depress the valve stem and release refrigerant from the container, the actuator including
an outlet tube for receiving the released refrigerant from the container; an inlet tube adapted to receive the valve stem therein; and
a main body which connects together said inlet tube and said outlet tube in fluid communication with each other, the main body including an arrangement for limiting insertion of the valve stem into the inlet tube, said main body further including
a generally cylindrical side wall,
a bottom wall which closes the side wall and which includes an opening, with the inlet tube and outlet tube being connected to opposite sides of the bottom wall in surrounding relation to the opening therein, and
a ledge connected with an upper edge of the side wall, the ledge defining an actuating surface against which at least one key engages, such that application of said pressure to the actuating surface causes said actuator to move such that the shoulder engages and depresses the valve stem to release the refrigerant;
a hub adapted to mount on the container, the hub including at least one opening therein and a first aligning arrangement;
an applicator tube mounted to the hub in fluid communication with the outlet tube of the actuator;
a porous tip mounted to a distal end of the applicator tube for receiving the refrigerant; and
a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant.

2. The cryosurgery device according to claim 1, wherein said main body further includes reinforcing ribs on an outer surface of the side wall and connected with said ledge.

3. A method of treating a skin lesion, comprising:
positioning a cryosurgery device, wherein in said device comprises:
an aerosol container for holding a refrigerant, the container including a valve and a valve stem extending out from the valve and the container;
an actuator seated on the valve stem in order to depress the valve stem and release the refrigerant from the container, the actuator including an outlet tube for receiving released refrigerant from the container;
a hub mounted on the container, the hub including at least one opening therein and a first aligning arrangement;
an applicator tube mounted to the hub in fluid communication with the outlet tube of the actuator;
a porous tip mounted to a distal end of the applicator tube for receiving the refrigerant; and
a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;
such that said base is below said container and said porous tip extends downwardly into said central opening of said base;
applying a force to said container, said base, or both, such that said at least one key enters said at least one opening in the hub to apply pressure to said actuator and cause refrigerant to be released into said applicator tube and porous tip;
discontinuing said force after said porous tip is chilled by liquid refrigerant to a therapeutically effective temperature;
removing said base; and
without removing said porous tip from said hub, promptly placing said chilled porous tip in contact with said skin lesion for a period of time sufficient to freeze said skin lesion, thereby treating said skin lesion.

4. A method of treating a skin lesion, comprising:
positioning a cryosurgery device, wherein said device comprises:
an aerosol container for holding a refrigerant, the container including a valve and a valve stem extending out from the valve and the container;
an actuator seated on the valve stem in order to depress the valve stem and release the refrigerant from the container, the actuator including an outlet tube for receiving released refrigerant from the container;
a hub mounted on the container, the hub including at least one opening therein and a first aligning arrangement; and
a base having a central opening for receiving the hub, the base including at least one key and a second aligning arrangement for cooperating with said first aligning arrangement such that the at least one key can enter the at least one opening in the hub to engage and apply pressure to the actuator to cause the actuator to depress the stem and release the refrigerant into the base;
such that said base is below said container and said hub extends downwardly into said central opening of said base;
applying a force to said container, said base, or both, such that said at least one key enters said at least one opening in the hub to apply pressure to said actuator and cause refrigerant to be released through said valve into said base;
discontinuing said force after a period of time sufficient to allow liquid refrigerant to collect in a pool in the base;
disconnecting said container from said base;
inserting an applicator device into said pool of liquid refrigerant for a period of time sufficient to chill said applicator device to a therapeutically effective temperature; and
promptly placing said chilled applicator device in contact with said skin lesion for a period of time sufficient to freeze said skin lesion, thereby treating said skin lesion.

5. A cryosurgery device for use with an aerosol container having a valve and a valve stem extending outwardly from the valve and the container, the container holding a refrigerant therein, the cryosurgery device comprising:
an actuator adapted to seat on a stem of a container in order to depress the valve stem and release refrigerant from the container, the actuator including an outlet tube for receiving the released refrigerant from the container;
a hub adapted to mount on the container, said hub includes:
a cylindrical side wall, and
a top wall which closes an upper end of said cylindrical side wall,
at least one opening is in said top wall;
an applicator tube mounted to the hub in fluid communication with the outlet tube of the actuator;
a porous tip mounted to a distal end of the applicator tube for receiving the refrigerant; and
a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;
wherein said first aligning arrangement includes at least one aligning rib on said cylindrical side wall, and said second aligning arrangement includes at least one recess for receiving the at least one aligning rib to angularly align the hub with the base.

6. A cryosurgery device for use with an aerosol container having a valve and a valve stem extending outwardly from the valve and the container, the container holding a refrigerant therein, the cryosurgery device comprising:
an actuator adapted to seat on a stem of a container in order to depress the valve stem and release refrigerant from the container, the actuator including an outlet tube for receiving the released refrigerant from the container;
a hub adapted to mount on the container, the hub including at least one opening therein and a first aligning arrangement;
an applicator tube mounted to the hub in fluid communication with the outlet tube of the actuator;
a porous tip mounted to a distal end of the applicator tube for receiving the refrigerant; and a base having a central opening for receiving the hub and applicator tube therein, wherein the opening in the base is closed by a lower wall at a lower end thereof; the base including at least one key and a second aligning arrangement for cooperating with said first aligning arrangement such that the at least one key can enter the at least one opening in the hub to engage and apply pressure to the actuator to cause the actuator to depress the stem and release the refrigerant.

7. A cryosurgery device for use with an aerosol container having a valve and a valve stem extending outwardly from the valve and the container, the container holding a refrigerant therein, the cryosurgery device comprising:
   an actuator adapted to seat on a stem of a container in order to depress the valve stem and release refrigerant from the container, the actuator including an outlet tube for receiving the released refrigerant from the container;
   a hub adapted to mount on the container, the hub including at least one opening therein and a first aligning arrangement;
   an applicator tube mounted to the hub in fluid communication with the outlet tube of the actuator;
   a porous tip mounted to a distal end of the applicator tube for receiving the refrigerant; and
   a base having a c6ntral opening for receiving the hub and applicator tube therein, the base including at least one key and a second aligning arrangement for cooperating with said first aligning arrangement such that the at least one key can
   enter the at least one opening in the hub to engage and apply pressure to the actuator to cause the actuator to depress the stem and release the refrigerant;
   wherein the base includes at least one inwardly extending projection, each having an upper surface on which one said key is mounted, and each said upper surface defining a limit as to an extent to which the hub can be inserted into said base.

8. A cryosurgery device for use with an aerosol container having a valve and a valve stem extending outwardly from the valve and the container, the container holding a refrigerant therein, the cryosurgery device comprising:
   an actuator adapted to seat on a stem of a container in order to depress the valve stem and release refrigerant from the container, the actuator including an outlet tube for receiving the released refrigerant from the container;
   a hub adapted to mount on the container, the hub including at least one opening therein and a first aligning arrangement;
   an applicator tube mounted to the hub in fluid communication with the outlet tube of the actuator;
   a porous tip mounted to a distal end of the applicator tube for receiving the refrigerant; and
   a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;
   wherein there are an equal number of said projections, keys of said base, and openings of said hub, said number being at least three.

9. A cryosurgery device comprising:
   an aerosol container for holding a refrigerant, the container including a valve and a valve stem extending out from the valve and the container;
   an actuator seated on the valve stem in order to depress the valve stem and release the refrigerant from the container, the actuator including an outlet tube for receiving released refrigerant from the container; an inlet tube connected with the main body and adapted to receive the valve stem therein; and
   a main body which connects together said inlet tube and said outlet tube in fluid communication with each other, the main body including:
      an arrangement for limiting insertion of the valve stem into the inlet tube; and an actuating surface against which at least one key engages, such that application of said pressure to the actuating surface causes said actuator to move such that the shoulder engages and depresses the valve stem to release the refrigerant;
      wherein said main body further includes:
      a generally cylindrical side wall,
      a bottom wall which closes the side wall and which includes an opening, with the inlet tube and outlet tube being connected to opposite sides of the bottom wall in surrounding relation to the opening therein, and
      a ledge connected with an upper edge of the side wall, the ledge defining said actuating surface;
   a hub mounted on the container, the hub including at least one opening therein and a first aligning arrangement;
   an applicator tube mounted to the hub in fluid communication with the outlet tube of the actuator;
   a porous tip mounted to a distal end of the applicator tube for receiving the refrigerant; and
   a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant.

10. A cryosurgery device comprising:
   an aerosol container for holding a refrigerant, the container including a valve and a valve stem extending out from the valve and the container;
   an actuator seated on the valve stem in order to depress the valve stem and release the refrigerant from the container, the actuator including an outlet tube for receiving released refrigerant from the container;
   a hub mounted on the container, the hub including at least one opening therein and a first aligning arrangement; wherein said hub includes:
      a cylindrical side wall, and
      a top wall which closes an upper end of said cylindrical side wail, and said at least one opening is in said top wall
   an applicator tube mounted to the hub in fluid communication with the outlet tube of the actuator;
   a porous tip mounted to a distal end of the applicator tube for receiving the refrigerant; and
   a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;
   wherein said container includes an upper annular lip and said hub further includes a securing arrangement at a lower end of said cylindrical side wall adapted to be snap-fit secured over the upper annular lip of the container;

wherein said first aligning arrangement includes at least one aligning rib on said cylindrical side wall, and the second aligning arrangement includes at least one recess for receiving the at least one aligning rib to angularly align the hub with the base.

11. A cryosurgery device comprising:

an aerosol container for holding a refrigerant, the container including a valve and a valve stem extending out from the valve and the container;

an actuator seated on the valve stem in order to depress the valve stem and release the refrigerant from the container, the actuator including an outlet tube for receiving released refrigerant from the container;

a hub mounted on the container, the hub including at least one opening therein and a first aligning arrangement;

an applicator tube mounted to the hub in fluid communication with the outlet tube of the actuator;

a porous tip mounted to a distal end of the applicator tube for receiving the refrigerant; and a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;

wherein the base includes at least one inwardly extending projection having an upper surface on which one said key is mounted, said upper surface defining a limit as to an extent to which the hub can be inserted into said base.

12. A cryosurgery device comprising:

an aerosol container for holding a refrigerant, the container including a valve and a valve stem extending out from the valve and the container;

an actuator seated on the valve stem in order to depress the valve stem and release the refrigerant from the container, the actuator including an outlet tube for receiving released refrigerant from the container;

a hub mounted on the container, the hub including at least one opening therein and a first aligning arrangement;

an applicator tube mounted to the hub in fluid communication with the outlet tube of the actuator;

a porous tip mounted to a distal end of the applicator tube for receiving the refrigerant; and a base having a central opening for receiving the hub and applicator tube therein, the base including at least one key and a second aligning arrangement for cooperating with said first aligning arrangement such that the at least one key can enter the at least one opening in the hub to engage and apply pressure to the actuator to cause the actuator to depress the stem and release the refrigerant;

wherein there are an equal number of said keys of said base and said openings in said hub, the number being at least three.

* * * * *